US009918654B2

(12) United States Patent
Grey et al.

(10) Patent No.: US 9,918,654 B2
(45) Date of Patent: *Mar. 20, 2018

(54) METHODS FOR ASSESSING AND OPTIMIZING MUSCULAR PERFORMANCE INCLUDING A FREQUENCY BASED, AMPLITUDE ADJUSTED ROOT MEAN SQUARE PROTOCOL

(71) Applicant: Somaxis Incorporated, San Jose, CA (US)

(72) Inventors: Alexander B Grey, Campbell, CA (US); Violetta Georgiou, Morgan Hill, CA (US); Abhishek Belani, Los Altos Hills, CA (US)

(73) Assignee: SOMAXIS INCORPORATED, San Jose, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 14/795,100

(22) Filed: Jul. 9, 2015

(65) Prior Publication Data

US 2015/0305672 A1 Oct. 29, 2015

Related U.S. Application Data

(62) Division of application No. 13/239,105, filed on Sep. 21, 2011, now Pat. No. 9,107,627.

(Continued)

(51) Int. Cl.
A61B 5/00 (2006.01)
A61B 5/0492 (2006.01)
(Continued)

(52) U.S. Cl.
CPC .......... A61B 5/0492 (2013.01); A61B 5/0006 (2013.01); A61B 5/0205 (2013.01);
(Continued)

(58) Field of Classification Search
CPC ....... A61B 5/04; A61B 5/0488; A61B 5/0205; A61B 5/224; A61B 5/01; A61B 5/112;
(Continued)

(56) References Cited

U.S. PATENT DOCUMENTS 6,440,067 B1 8/2002 DeLuca et al.
6,859,663 B2 2/2005 Kajitani et al.
(Continued)

FOREIGN PATENT DOCUMENTS

WO 97-13454 A1 4/1997

OTHER PUBLICATIONS

International Search Report dated Apr. 19, 2012 as received in application No. PCT/US2011/052649.
(Continued)

Primary Examiner — Max Hindenburg
(74) Attorney, Agent, or Firm — Alpine IP PLLC

(57) ABSTRACT

A muscle assessment protocol can include: attaching one or more surface electromyometry (sEMG) sensors to the skin of a subject to be operably coupled with one or more muscles; operably coupling the one or more sEMG sensors to a computing system; performing the predetermined muscle activity of a muscle assessment protocol that includes a frequency-based, amplitude-adjusted root mean square protocol; monitoring/recording sEMG data of the one or more muscles during the predetermined muscle activity; and providing the sEMG data to the subject such that the subject can improve muscle performance for the predetermined muscle activity by using the sEMG data. The muscle activity includes static or dynamic muscle use. The predetermined muscle activity can be provided to the subject by the computing system.

22 Claims, 16 Drawing Sheets

Related U.S. Application Data

(60) Provisional application No. 61/385,046, filed on Sep. 21, 2010, provisional application No. 61/385,038, filed on Sep. 21, 2010, provisional application No. 61/385,048, filed on Sep. 21, 2010, provisional application No. 61/385,053, filed on Sep. 21, 2010, provisional application No. 61/385,049, filed on Sep. 21, 2010, provisional application No. 61/385,051, filed on Sep. 21, 2010, provisional application No. 61/514,148, filed on Aug. 2, 2011.

(51) Int. Cl.
| | | |
|---|---|---|
| *A61B 5/22* | (2006.01) | |
| *A61B 5/11* | (2006.01) | |
| *A61B 5/0402* | (2006.01) | |
| *A61B 5/0408* | (2006.01) | |
| *A61B 5/0205* | (2006.01) | |
| *A61B 5/0488* | (2006.01) | |
| *G06F 19/00* | (2018.01) | |
| *A61B 5/04* | (2006.01) | |
| *A61B 5/01* | (2006.01) | |

(52) U.S. Cl.
CPC .......... *A61B 5/0402* (2013.01); *A61B 5/0408* (2013.01); *A61B 5/04012* (2013.01); *A61B 5/0488* (2013.01); *A61B 5/112* (2013.01); *A61B 5/222* (2013.01); *A61B 5/224* (2013.01); *A61B 5/486* (2013.01); *A61B 5/4866* (2013.01); *A61B 5/6801* (2013.01); *A61B 5/6833* (2013.01); *A61B 5/725* (2013.01); *A61B 5/7235* (2013.01); *A61B 5/7246* (2013.01); *A61B 5/7275* (2013.01); *A61B 5/746* (2013.01); *G06F 19/345* (2013.01); *G06F 19/3481* (2013.01); *A61B 5/01* (2013.01); *A61B 2503/10* (2013.01); *A61B 2560/0223* (2013.01); *A61B 2560/0238* (2013.01); *A61B 2560/0412* (2013.01); *A61B 2562/164* (2013.01)

(58) Field of Classification Search
CPC ... A61B 5/0402; A61B 5/0408; A61B 5/4866; A61B 5/0492; A61B 5/222; A61B 5/6833; A61B 2503/10; A61B 2560/0223; A61B 2560/0238; A61B 2560/0412; A61B 2562/164
USPC .......................................................... 600/546
See application file for complete search history.

(56) References Cited

U.S. PATENT DOCUMENTS

| | | |
|---|---|---|
| 6,965,794 B2 | 11/2005 | Brody |
| 7,433,733 B2 | 10/2008 | Endo et al. |
| 7,634,311 B2 | 12/2009 | Blomberg et al. |
| 7,764,990 B2 | 11/2010 | Martikka et al. |
| 7,828,753 B2 | 11/2010 | Euliano et al. |
| 2008/0058668 A1 | 3/2008 | Seyed Momen et al. |

OTHER PUBLICATIONS

Written Opinion of the International Searching Authority dated Apr. 19, 2012 as received in application No. PCT/US2011/052649.

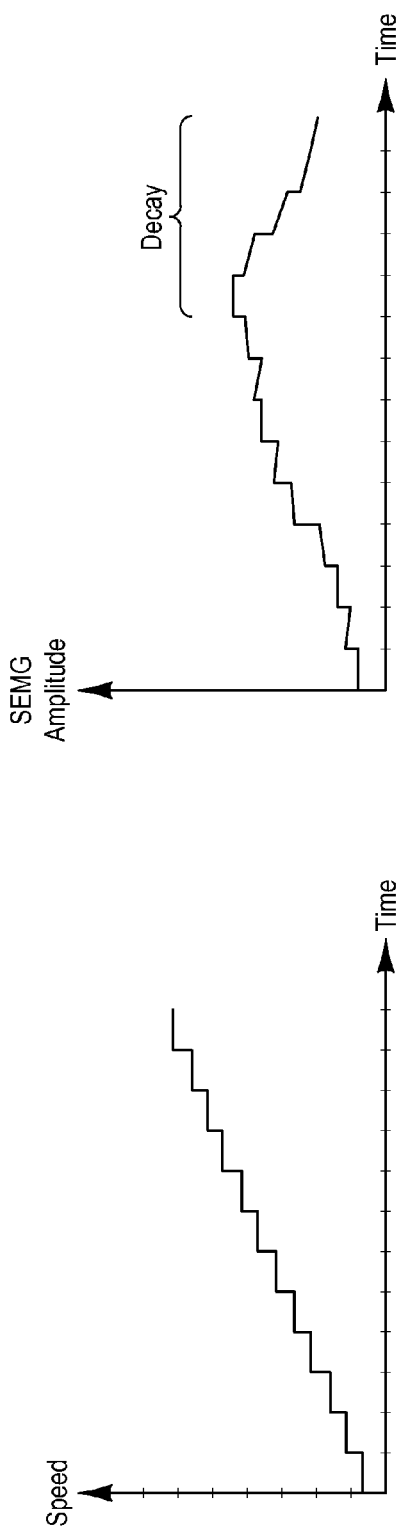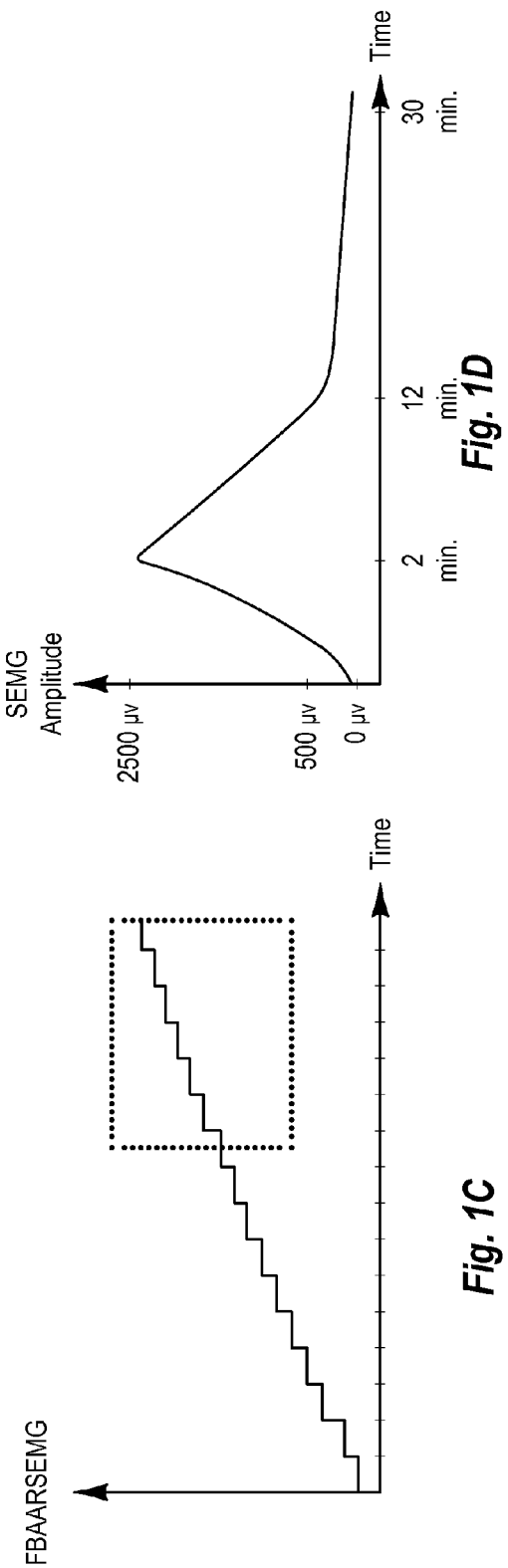

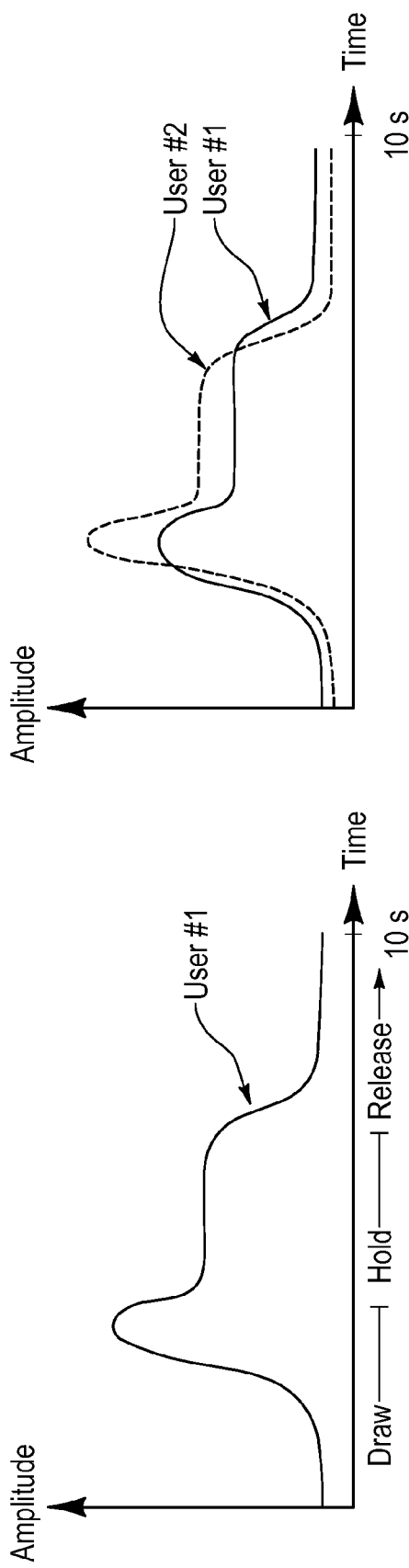
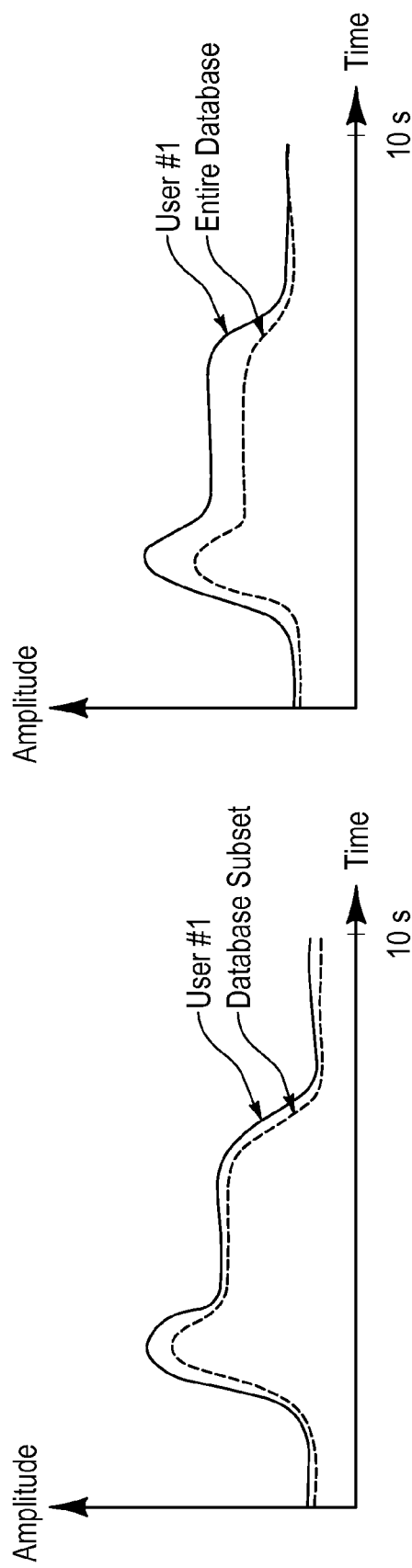
Fig. 3A
Fig. 3B
Fig. 3C
Fig. 3D

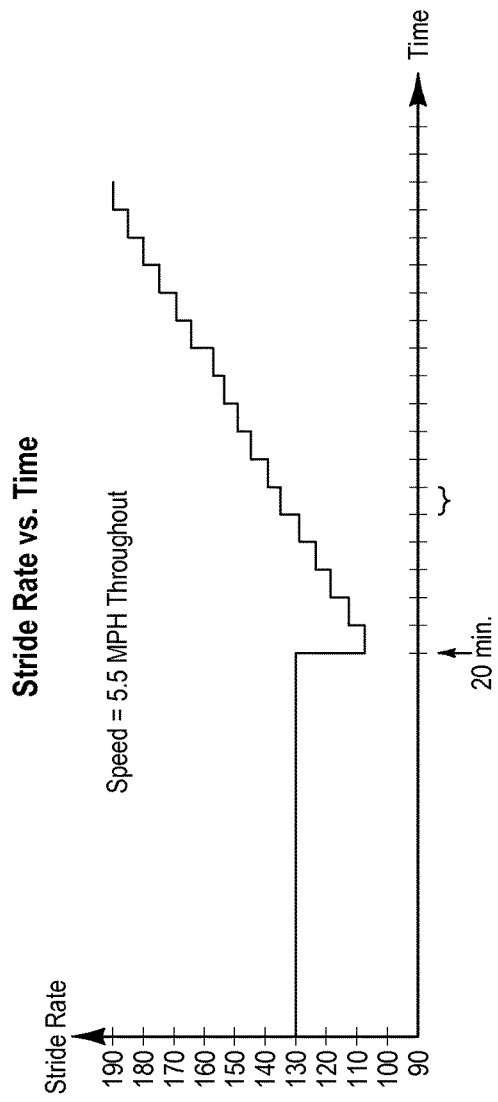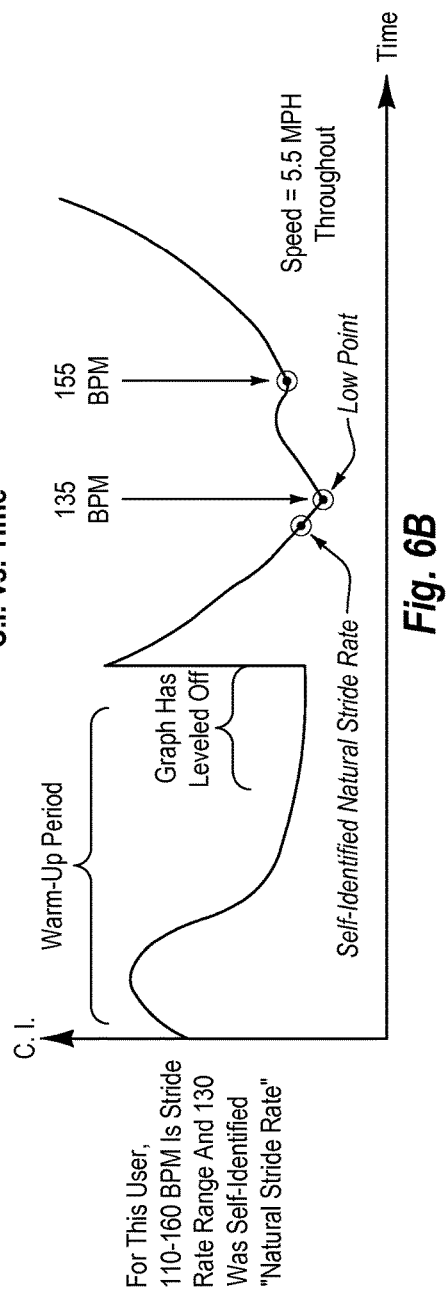

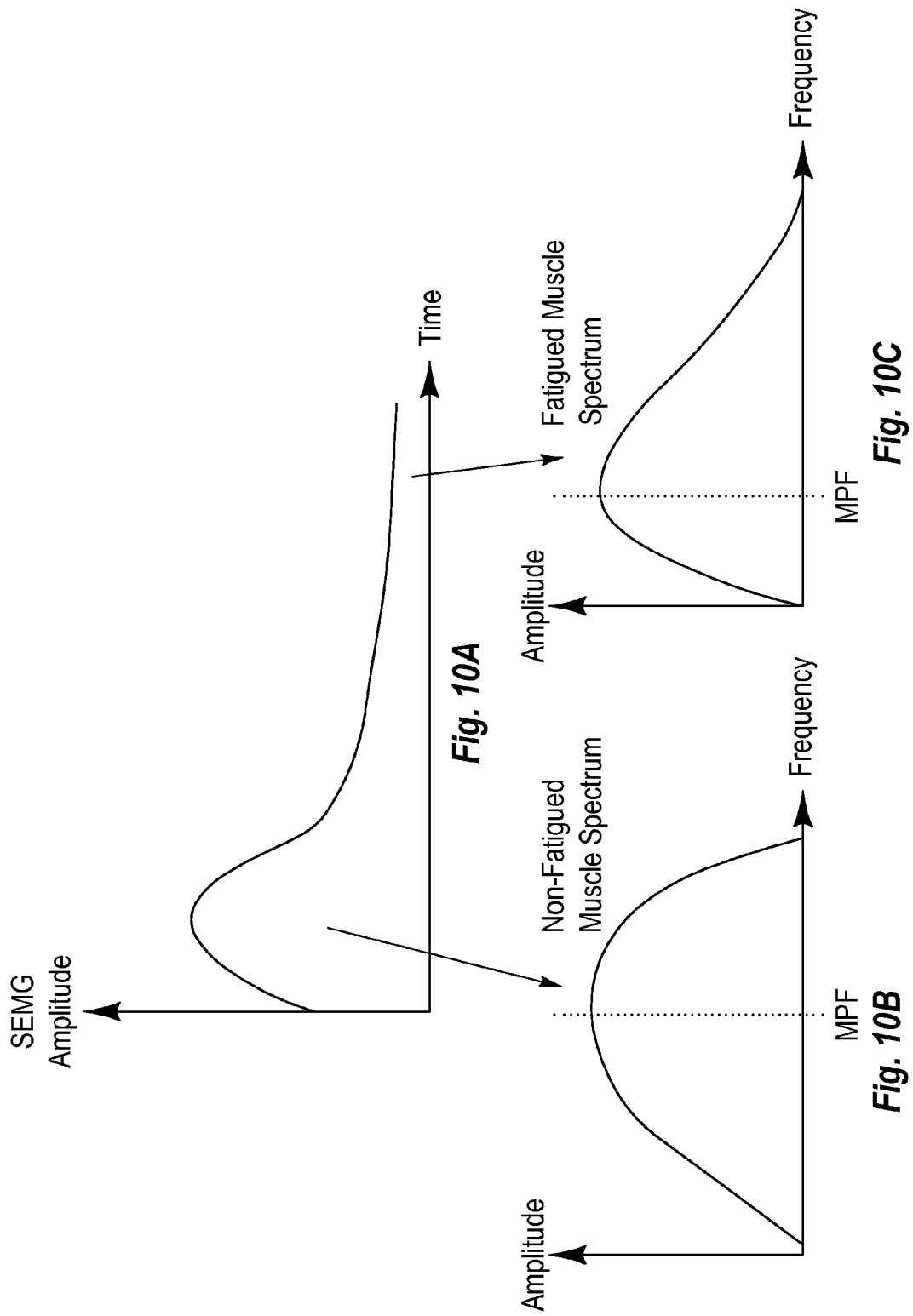

METHODS FOR ASSESSING AND OPTIMIZING MUSCULAR PERFORMANCE INCLUDING A FREQUENCY BASED, AMPLITUDE ADJUSTED ROOT MEAN SQUARE PROTOCOL

CROSS-REFERENCE TO RELATED APPLICATIONS

This patent application is a division of U.S. patent application Ser. No. 13/239,105 filed on Sep. 21, 2011, which claims the benefit of U.S. Provisional Application Nos. 61/385,046, 61/385,038, 61/385,048, 61/385,049, 61/385,051, and 61/385,053 all of which provisional applications were filed on Sep. 21, 2010. In addition, this patent application claims the benefit of U.S. Provisional Application No. 61/514,148, filed Aug. 2, 2011. All of the aforementioned provisional and non-provisional patent applications are incorporated herein by specific reference in their entirety.

BACKGROUND

Generally, there are various methods for monitoring and analyzing muscle condition and/or performance. Often, such muscle monitoring and analysis involves some form of myometry, which measures the strength of a muscle by measuring the force that the muscle can generate. For an example of myometry, a user squeezes a device which in turn measures and transmits force information back to a computer, and the computer computes a force/time curve. The measurement is usually via electronic components, and thereby can be referred to as electromyometry. These electronic devices are typically fully wired systems that require immediate proximity to a computer, and which are designed to be operated by physicians or clinicians in appropriate controlled settings.

Surface electromyometry (sEMG) is a type of myometry that uses surface sensors to obtain information about the functionality of one or more muscles during a muscular activity. The sEMG assessments can be sorted into three general groups of muscle activity: static muscle activity, dynamic muscle activity, or combination of static and dynamic muscle activities. The different muscle activity paradigms can be useful for different muscle assessments.

A static muscle activity may occur with no load (i.e. sitting) or with an isometric load (no movement of limb). Static muscle activity evaluation can include observation of the rectified amplitude of the sEMG data. The static muscle activity evaluation can be useful for a specific muscle or muscle group or as a comparison to other muscles or muscle groups. Absolute levels of the sEMG data can be monitored through root mean square of the sEMG amplitude (e.g., RMS sEMG amplitude), and abnormally large values of the RMS sEMG can be identified or determined. Rhythmic contraction patterns of the muscle or muscle groups can be identified or determined, and may also be based on rectified amplitude. During an isometric loading protocol, a user can exert an amount of force while keeping the limb fixed in a single position. Usually, the force exerted is measured as a fixed percentage of Maximum Voluntary Contraction (MVC). Then, the median frequency (MF) or mean power frequency (MPF) can be measured or determined by observing or analyzing the frequency spectrum of the sEMG. In this manner, the fatigue level of the muscles can be established, and the point at which fatigue begins to occur may be identified.

Dynamic muscle activity evaluations can ascertain relationships between sEMG amplitude and force, which have been shown to be "curvilinear", or non-linear at the extremes of the force range (e.g., very little force, or a lot of force) and essentially linear for the majority of the force/amplitude relationship. Evaluating that relationship is useful for dynamic muscle activity sEMG evaluation. Methods for implementing dynamic muscle activity evaluations can include incrementally increasing the force exerted by the muscle by way of a machine that measures force, and measuring the sEMG amplitude of the muscle activity that is associated with various force levels. Dynamic muscle activity evaluations can be used in the evaluation of torque and paralysis. There are dynamic muscle activity evaluation methods for: muscle imbalance, trigger points, cocontractions, and fasciculations.

However, the abovementioned muscle assessment methods can be used to assess a variety of pathologies and physiological states which may correspond to (or attempt to correspond to) clinical and/or medical conditions. These methods have typically been designed to be performed by specialists (e.g., MD, chiropractor, physical therapist, etc.). However, these muscle assessment methods are usually restricted to controlled settings in the presence of these specialists. Thus, there is not a way for a common person to implement muscular assessment on their own. Therefore, there remains a need to bring the ability to implement muscle assessment to the masses.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1A includes a graph that illustrates speed versus time of a subject during a muscleprint exercise routine that is conducted as a "step-up test," where the exercise can be walking, jogging, running, cycling, or the like;

FIG. 1B includes a graph that illustrates surface electromyography (sEMG) amplitude versus time with a decay period later in time of a subject during a muscleprint exercise routine that is conducted as a "step-up test;"

FIG. 1C includes a graph that illustrates frequency-based, amplitude-adjusted RMS sEMG versus time with a decay period (e.g., RMS of decay in dashed box) later in time of a subject during a muscleprint exercise routine that is conducted as a "step-up test;"

FIG. 1D includes a graph that illustrates sEMG amplitude (e.g., microV) versus time (e.g., minutes) of a subject during a muscleprint exercise routine that is conducted as a "step-up test," with speed constant with respect to time;

FIG. 3A includes a graph that illustrates sEMG amplitude versus time of a subject during a muscleprint exercise routine that has an action-hold-release protocol, and is exemplified by a using a bow to draw-hold-release;

FIG. 3B includes a graph that illustrates sEMG amplitude versus time of two different subjects during a muscleprint exercise routine that has an action-hold-release protocol, and is exemplified by a using a bow to draw-hold-release;

FIG. 3C includes a graph that illustrates sEMG amplitude versus time of a subject compared to a database of subjects (e.g., similar subjects in size, weight, height age, condition, etc.) during a muscleprint exercise routine that has an action-hold-release protocol, and is exemplified by a using a bow to draw-hold-release;

FIG. 3D includes a graph that illustrates sEMG amplitude versus time of a subject compared to an entire database of subjects during a muscleprint exercise routine that has an action-hold-release protocol, and is exemplified by a using a bow to draw-hold-release;

FIG. 4A includes a graph that illustrates sEMG amplitude versus time, where the sEMG amplitude is a metric observed during a muscleprint exercise routine such as walking, jogging, running, cycling, or the like;

FIG. 4B includes a graph that illustrates sEMG amplitude versus time, where the sEMG amplitude is an average rectified amplitude during a muscleprint exercise routine such as walking, jogging, running, cycling, or the like;

FIG. 4C includes a graph that illustrates sEMG amplitude versus time, where the sEMG amplitude is an integrated sEMG or area under curve of FIG. 4A during a muscleprint exercise routine such as walking, jogging, running, cycling, or the like;

FIG. 4D includes a graph that illustrates mean power frequency (i.e., MPF) versus time, where the MPF may be a mean power frequency variance observed during a muscleprint exercise routine such as walking, jogging, running, cycling, or the like;

FIG. 4E includes a graph that illustrates mean power frequency (i.e., MPF) versus time, where the MPF may be a mean power frequency variance observed during a muscleprint exercise routine such as "step-up test" routine or weightlifting routine or the like;

FIG. 4F includes a graph that illustrates RMS sEMG versus time or frequency-based, amplitude-adjusted RMS sEMG versus time (i.e., FBAAR v. time) during a muscleprint exercise routine such as walking, jogging, running, cycling, or the like;

FIG. 6A includes a graph that illustrates stride rate versus time, where speed is constant throughout exercise routine at 5.5 MPH, where stride rate is held constant up to 20 minutes and then initially decreased before being increased in a "step-up test;"

FIG. 6B includes a graph that illustrates cumulative integral versus time for FIG. 6A, where speed is constant throughout exercise routine at 5.5 MPH in a "warm-up period;"

FIG. 8C is an alternative profile compared to FIG. 8B;

FIG. 10A includes a graph similar to FIG. 8A;

FIG. 10B includes a graph that illustrates sEMG amplitude versus frequency for a non-fatigued muscle spectrum from FIG. 10A, and shows the MPF;

FIG. 10C includes a graph that illustrates sEMG amplitude versus frequency for a fatigued muscle spectrum from FIG. 10A, and shows the MPF;

DETAILED DESCRIPTION

Figure 2A:
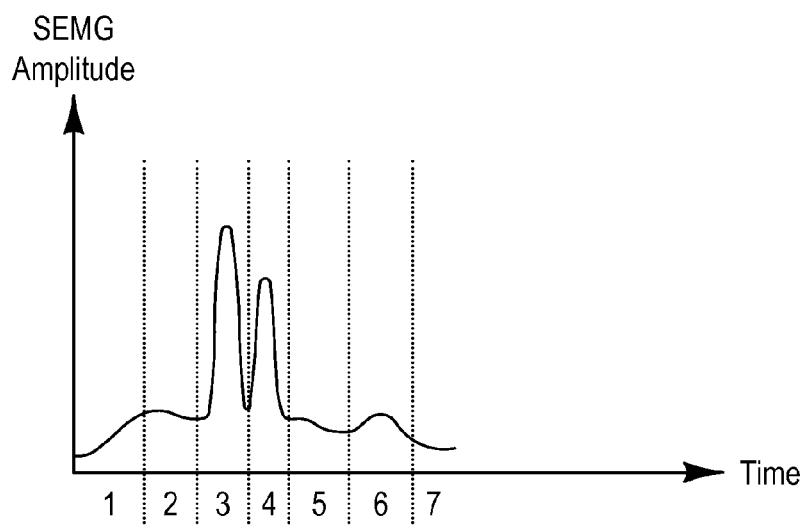
FIG. 2A includes a graph that illustrates sEMG amplitude versus time (e.g., arbitrary unit) of a subject during a muscleprint exercise routine that is conducted as a "step-up test," where Period (1) indicates a "transition" (e.g., from standing to full squat), Period (2) indicates being "stationary" (e.g., staying in squat before a jump), Period (3) indicates a "transition" (e.g., jumping up), Period (4) indicates a "transition" (e.g., absorbing impact or weight or force of landing from jump), Period (5) indicates being "stationary" (e.g., staying in squat before rising), and Period (6) indicates a "transition" (e.g., rise to standing)

Embodiments In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes systems and methods for implementing muscle assessment protocols. The assessment protocols can be implemented in a manner such that a common person can obtain accurate muscle information. The inventive muscle assessment protocols can be implemented with the aide of computing systems and software with user interfaces to facilitate use by a common person. The muscle assessment protocols can be implemented without controlled settings or specialists. As such, the muscle assessment protocols described herein may be useful for monitoring and analyzing muscle function of healthy individuals, and therefore may not be used in connection with determination or monitoring of disease states. The muscle assessment protocols can be used for personal use, which may include analysis of an exercise routine as well as the musculature benefits, improvements, or declines that may occur. The muscle assessment protocols can be used to monitor and analyze muscular performance of an athletic subject who already is relatively healthy, but who may desire improvement in their overall health or athletic performance, or general muscle maintenance.

The muscle assessment protocols can be designed and implemented for the assessment of muscular performance for athletic consumers. These protocols differ from standard medical and clinical assessment techniques in a variety of ways. One example of a differentiating factor is that the inventive muscle assessment protocols are designed for implementation that is automatic and software-driven. Ease of use allows any subject to receive the benefit of muscle assessment. Another distinguishing factor includes the inventive muscle assessment protocols being designed and implemented as standard actions for a wide variety of different muscle activities for one or more muscles, exercise disciplines, of for one or more specific muscles. Also, the muscle assessment protocols can be performed by a common person without specific equipment other than one or more sensors that can be worn on the subject as well as a computing system for measuring, recording, and analyzing the data obtained during the protocol. This differs from the strategy of an assessor having a number of different assessment tools at their disposal, and relying upon judgment to determine which is best for a particular individual (typically, with the goal of diagnosis in mind).

The muscle assessment protocols can use computing systems and software for measuring, recording, and analyzing the data from the subject having their muscles being assessed. The protocols can focus on single muscle or muscle group performance assessment from the perspective of basic muscle functional through muscle performance enhancement as well as optimization of muscular performance. The protocols can be implemented with one or more muscles for short and/or long periods of physical exertion in static, dynamic and/or combined static and dynamic muscle activities.

Figure 12:
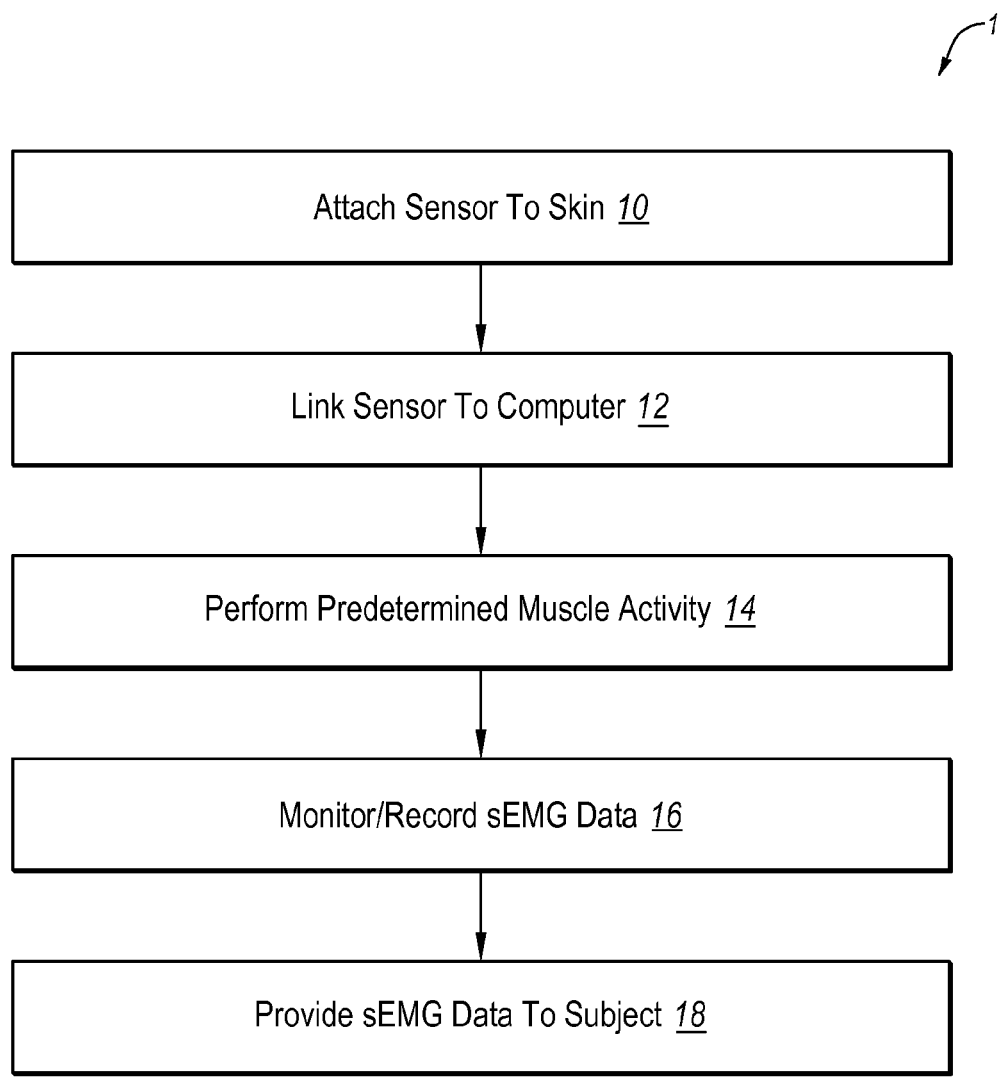
FIGS. 12-15 include flow diagrams for different methods, which can be performed as described herein, where one or more steps may be omitted, arranged in accordance with at least one of the embodiments described herein, and which arrangement may be modified in accordance with the disclosure provided herein by one of ordinary skill in the art.

In one embodiment, the present invention provides a method for performing a muscle assessment protocol. FIG. 12 illustrates an embodiment of a method for performing the muscle assessment protocol 1, which can include: attaching one or more surface electromyometry (sEMG) sensors to the skin of a subject so as to be operably coupled with one or more muscles of the subject (Attach Sensor to Skin," block 10); operably coupling the one or more sEMG sensors to a computing system ("Link Sensor to Computer," block 12); performing the predetermined muscle activity of a muscle assessment protocol ("Perform Predetermined Muscle Activity," block 14) that includes one or more of a muscleprint protocol, stride rate tuning protocol, controlled activity training protocol, or frequency-based, or amplitude-adjusted root mean square protocol; monitoring and/or recording sEMG data of the one or more muscles during the predetermined muscle activity ("Monitor/Record sEMG Data," block 16); and providing the sEMG data to the subject such that the subject can improve muscle performance for the predetermined muscle activity by using the sEMG data ("Provide sEMG Data to Subject," block 18). The muscle activity includes static (e.g., resistance against a load) or dynamic muscle use. The predetermined muscle activity can be provided to the subject by the computing system. The muscle activity can include a continuous exercise routine or a noncontinuous exercise routine. The continuous exercise routine can include one or more of walking, jogging, running, sprinting, hiking, cycling, rollerblading, roller skating, skiing, cross-country skiing, rowing, swimming, snowboarding, yoga, pilates, and the like. The noncontinuous exercise routine can include one or more of firing an arrow from a bow, weightlifting, golf swing, bat swing, ball throw, punch, kick, jumping, squatting, or the like.

The muscle assessment protocols can include a series of assessed activities that provide data that can be analyzed in order to provide a subject with a better understanding of the muscular activity and response patterns. Once a muscle response pattern can be determined, then strategies can be implemented so that optimal muscle performance can be targeted and hopefully achieved. The muscle assessment protocols can be described as: a muscleprint protocol; a stride rate tuning protocol; a controlled activity training protocol, or a frequency-based, amplitude-adjusted root mean square protocol. A muscleprint is a muscle assessment protocol that monitors muscle sEMG data of a muscular response while a subject is engaged in an activity. In the muscleprint protocol, the one or more sensors each monitor muscle sEMG data of the one or more muscles while the subject performs the predetermined activity in order to determine the subject's muscular capabilities of the one or more muscles over a defined period of time or portion thereof. Stride rate tuning is a muscle assessment protocol that monitors muscle sEMG data while a subject adjusts their caloric expenditure during a controlled activity based on sEMG data measure and analyzed, and then provided back to the subject during the protocol. In the stride rate tuning protocol, the one or more sensors monitor muscle sEMG data while the subject adjusts their caloric consumption during a controlled activity based on sEMG data that is measured and/or analyzed, and the sEMG data is provided to the subject in order to facilitate the adjustment of caloric consumption. Controlled activity training is a muscle assessment protocol where an sEMG metric or a derivative metric is kept constant during a particular physical activity and a non-quantitative, athletic activity is varied, which allows for precise training based on a quantitative metrics while engaged in inherently subjective activities. In the controlled activity training protocol, the subject maintains substantially a constant sEMG metric or metric derivative or metric integral by varying muscle activity exertion during the predetermined muscle activity. Frequency-based, amplitude-adjusted root mean square is a muscle assessment protocol that provides for displaying sEMG data that is adjusted to compensate for fatigue (e.g., frequency-based) muscle signal dropout. In the frequency-based, amplitude-adjusted root mean square that includes displaying sEMG data that is adjusted to compensate for muscle fatigue of the one or more muscles.

The sEMG data can include a metric selected from: sEMG amplitude; instantaneous rectified sEMG amplitude; average rectified sEMG amplitude; area under sEMG curve; area over sEMG curve; integrated sEMG; derivative sEMG; frequency-based, amplitude adjusted RMS sEMG; mean power frequency (MPF); muscle fatigue onset index (MFOI); or combination thereof.

One implementation of the invention can be to compare different results of the same subject from a muscle activity performed at different times. Another implementation can be to compare different results of the same muscle activity across multiple subjects. Traditionally, the subjects are human, but the principle can be applied to non-human subjects, such as dogs, horses, or the like. When comparing the data for a muscle activity or the results of the muscle activity, the data can be normalized with respect to the muscle activity. The normalization can be on speed, repetitions, or other parameter of the muscle acidity. With running as an example, the comparative relationships and amplitude levels of the data can be linked to a particular speed. As such, normalization of the data can be performed before the comparison of the data so that the data is relevant across the subjects. The normalization can adjust the levels to compare them as if they were recorded at the same speed.

In one embodiment, muscle data can be used to create a reference database. The database can include various types of muscle data, such as the data described herein or the metrics of the data described in the incorporated references. For example, the database can include RMS EMG data and frequency values for people of different age, sexes, shapes, size, BMI, and athletic condition. For example, the speed of a run can be a parameter in the database. The database can include muscle data for all muscle optimization protocols described herein. The data can be raw data or normalized data.

In one example, the database can be used to compare different subjects. The subjects can include a 25-year old man who is 6'5" with 4% body fat, and a 80-year old woman who is 4'11" with 18% body fat. It is likely that these individuals do not perform muscle activities at the same level, and as such, the data or data values need to be normalized before being compared. The computing system associated with the database can facilitate adjustment of the recorded values between different subjects in order to estimate what the values would be if they had the same age, sex, BMI, and activity speed.

The database can be used to provide data and information as well as to receive data and information. The data can be used for direct or normalized comparison between subjects. For example, the first time a run or test is performed by a subject and some kind of metric is produced, comparisons and adjustments can be made to a reference database of people with similar age, sex, BMI, and activity speed. In another example, if the user has never recorded a MVC or "pseudo-MVC" type of exercise, then these levels can be taken from a reference database. Subsequent to initial tests, such as including MVC, pseudo-MVC, and any of the muscleprinting methods, the initial results can also be used in addition to the reference database values for additional accuracy.

Muscleprint

Generally, the muscleprinting muscle assessment protocol can be designed to determine a subject's muscular capabilities during a muscle activity over a defined period of time in order to identify or determine a muscle sEMG profile in response to the muscle activity. The defined period of time can vary, and a portion or the whole time can be used. Much like a fingerprint, a muscleprint is a unique snapshot of an individual's personal biometric characteristics for the given period of time. Unlike a fingerprint, a muscleprint may change for an individual over time as the individual gets into better shape or as physiological changes occur for the individual. Also unlike a fingerprint, a muscleprint cannot be used for identification purposes due to the ever changing muscle conditions and responses to the same or different activity. While muscleprinting can be used for common athletic activities, it can also be used for any activity that uses a muscle that is static (e.g., loaded) or dynamic.

Muscleprinting may be accomplished in a variety of ways. In one aspect, a muscleprinting protocol can be implemented with a "step-up test" for a continuous or noncontinuous muscular activity. A particularly useful continuous muscular activity for muscle printing is running because it can result in the onset of fatigue before other similar activities, which results in a shorter assessment period of time. FIG. 1A includes a graph that illustrates speed versus time of a subject during a muscleprint exercise routine that is conducted as a "step-up test." For a running example, a treadmill can be used when programed to incrementally increase the speed at defined time intervals. For example, the speed of the treadmill can be increased by 0.25 MPH for a defined period of time, such as 20 seconds. Examples of speed increases can be 0.5 MPH, 1 MPH, 2 MPH, 3 MPH, 4 MPH, or higher for fit athletes. For continuous muscular activities such as cycling where the rate is much faster, the speed increases can be multiplied by a factor, such as a factor of 5 or 10 depending on the fitness level of the subject. The time period can vary greatly, where the time period can be as short as 20 to 30 seconds or as long as 10 minutes depending on the particular activity. For example, running activities can have shorter periods between step-up increases in speed, while cycling activities can have longer periods between step-up increases. The protocol can also be implemented with a subject that is capable of monitoring their speed and then increasing their speed by increments after defined time periods. In an actual experimental protocol, the step-up-test was structured as follows: run at 1.0 MPH for a first period of 3 minutes; run at 1.5 MPH for a second period of 3 minutes; run at 2.0 MPH for a third period of time for 3 minutes; and so on at 0.5 MPH increments until 8.0 MPH or as fast as the subject can run in a sprint, or until fatigued. When step-up increments result a final speed of 8.0 MPH, the total duration of the step-up test can be 45 minutes.

FIG. 1B includes a graph that illustrates another example of surface electromyography (sEMG) amplitude versus time study with a decay period later in time of a subject during a muscleprint exercise routine that is conducted as a "step-up test." The metric observed and recorded for each section of the run was the average rectified sEMG amplitude. As shown in FIG. 1B, each step-up occurs, but the sEMG amplitude can vary between each step. This can be a result of some fatigue or other reason why the subject cannot maintain the identified speed. Accordingly, the graph in FIG.

1B can be obtained from the sEMG that was recorded from the speed step-up of FIG. 1A.

FIG. 1C includes a graph that illustrates frequency-based, amplitude-adjusted RMS sEMG versus time with a decay period (e.g., RMS of decay in dashed box) later in time of a subject during a muscleprint exercise routine that is conducted as a "step-up test." This graph can be generated from the data of FIG. 1B.

There are a number of other types of muscleprinting algorithms which can be implemented. A muscle printing algorithm can be determined to depend on the type of athletic activity. For instance, there is the "typical run" muscleprint for runners as shown in FIG. 1D. FIG. 1D includes a graph that illustrates sEMG amplitude (e.g., microV) versus time (e.g., minutes) of a subject during a muscleprint exercise routine that is conducted as a "step-up test," with speed constant with respect to time. One implementation of this method would require a runner to run for 30 minutes at 5.0 MPH with a constant neutral stride rate, which results in the change in sEMG amplitude over time. Also, the rate and duration can be modulated depending on the subject.

In another example, a muscleprint protocol can include the activity of a transition muscle activity and then a stationary muscle activity, or vice versa. Also, the activity can include a first transition muscle activity, a first stationary muscle activity, a second transition muscle activity, and then a second stationary activity. The activity may also be a transition muscle activity, a stationary muscle activity, a second transition muscle activity, a third transition activity, and then a second stationary activity. Accordingly, various combinations and arrangements of stationary and transition muscle activities can be implemented. The transition activity can include squatting down, the stationary muscle activity can be staying squatted or otherwise waiting for the next transition activity. Generally, the stationary muscle activities do not involve movement or change in position, while the transition muscle activities include active motion or movement or changing position. One example can include holding a squat for a stationary muscle activity and then jumping straight up into the air as high as possible with a stationary squat between each jump for a defined number of times, such as 3 times, 5 times, 7 times, or 9 times in a row or any number therebetween. These types of muscle activities can be described as noncontinuous due to the way the muscle activity is implemented not being continuous.

FIG. 2A includes a graph that illustrates sEMG amplitude versus time (e.g., arbitrary unit) of a subject during a muscleprint exercise routine that is conducted as a "step-up test," where Period (1) indicates a "transition" (e.g., from standing to full squat), Period (2) indicates being "stationary" (e.g., staying in squat before a jump), Period (3) indicates a "transition" (e.g., jumping up), Period (4) indicates a "transition" (e.g., absorbing impact or weight or force of landing from jump), Period (5) indicates being "stationary" (e.g., staying in squat before rising), and Period (6) indicates a "transition" (e.g., rise to standing).

Additionally, step-up tests can be performed with noncontinuous athletic activities. Examples of noncontinuous athletic activities include weightlifting, throwing, kicking, punching, golfing, tennis, or others that have start-stop motions. Accordingly, weightlifting is a good example of a noncontinuous athletic activity can be performed during a muscleprint protocol. Weightlifting can be conducted with the step-up test as well by using progressively heavier weights for a specific exercise such as biceps curls. For example, the weight can be increased in increments of 5 pounds until exhaustion or a predefined weight limit, and certain measurements can be made, such as sEMG, at each weight increment. The increase in rate or weight or resistance can be described as an increase in muscle output or muscle effort. The sEMG data can be processed for rectified amplitude and/or mean power frequency (i.e., MPF) during max amplitude of repetition of lifting the weight. This can allow for a muscleprint similar to the one developed for running, a step-up test described above for weightlifting or other noncontinuous muscle activities.

Figure 2B:
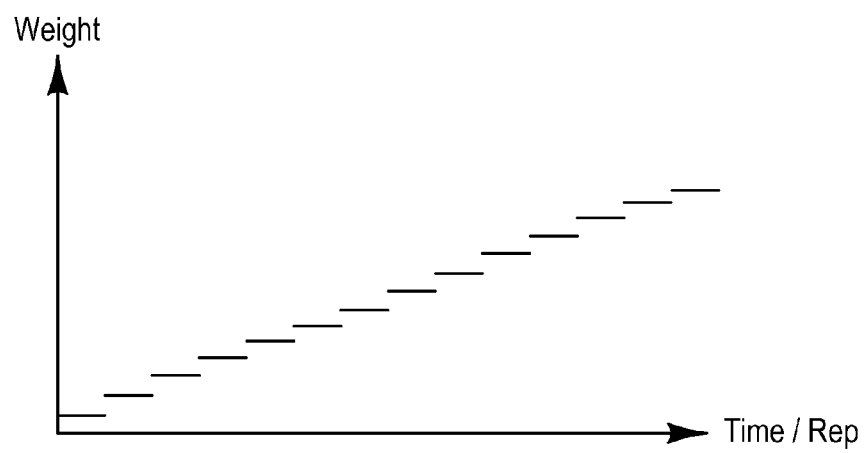
FIG. 2B includes a graph that illustrates weight versus time per rep (i.e., time/rep) of a subject during a muscleprint weightlifting exercise routine that is conducted as a weightlifting "step-up test," where each horizontal line represents a 5 pound increment increase, and while the weightlifting exercise routine can be a machine bench press, any weight lifting exercise can be conducted ant the weight increment increase can vary.
Figure 2C:
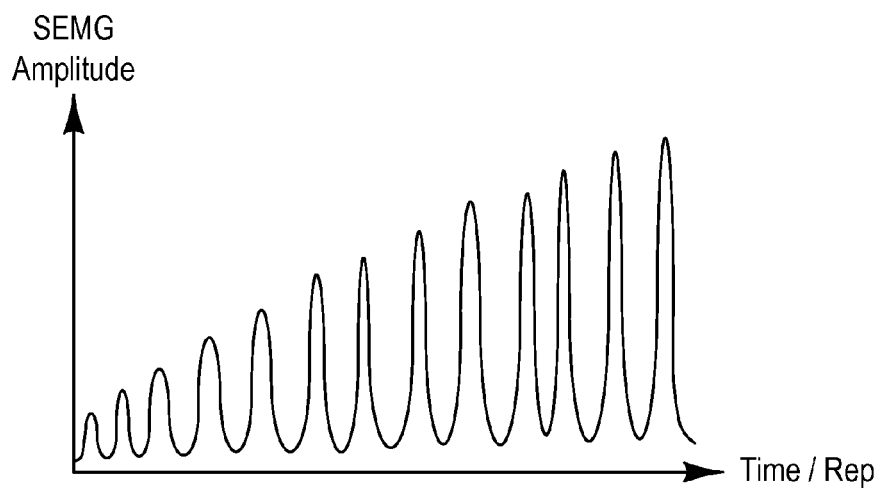
FIG. 2C includes a graph that illustrates sEMG amplitude versus time per rep (i.e., time/rep) of a subject during a muscleprint weightlifting exercise routine that is conducted as a weightlifting "step-up test,"

FIG. 2B includes a graph that illustrates weight versus time per rep (i.e., time/rep) of a subject during a muscleprint weightlifting exercise routine that is conducted as a weightlifting "step-up test," where each horizontal line represents a 5 pound increment increase, and while the weightlifting exercise routine can be a machine bench press, any weight lifting exercise can be conducted ant the weight increment increase can vary. FIG. 2C includes a graph that illustrates sEMG amplitude versus time per rep (i.e., time/rep) of a subject during a muscleprint weightlifting exercise routine that is conducted as a weightlifting "step-up test."

The muscleprinting protocol can be implemented by processing data through the proper algorithm. As such, the subject of the muscleprinting protocol can wear a device that records sEMG data, and the device can be configured to record sEMG output during all phases of muscleprinting activities. This allows for the muscleprinting protocol to both facilitate a specific exercise plan, recordation of sEMG data during the exercise plan, and process the data to provide a subjective analysis of the subject's muscleprint. The muscleprint can then be used for analysis and strategizing exercise routines to improve muscle condition and function.

In one embodiment, the muscleprinting protocol can be used to record quantitative biometric data (e.g., sEMG) in a standardized method to allow for comparisons to be made across time for a single individual, between different individuals, between an individual and a database of metrics taken for a subset of a large population, or compared to the entire database. The data obtained during a muscleprinting protocol can then be input into a computing method for an automatic software-driven assessment of an individual's muscular capabilities and a comparative analysis can be performed between the individual's data and the data of one or more other individuals. These comparisons can result in data that can be provided to the individual in a manner that allows for visual comparison of the performance data. The data can be illustrated for the individual in a table, graph, or other visual display. Also, the data may be converted to audio and played so that the individual can listen to the results. The comparisons can be implemented for any type of continuous or noncontinuous athletic activity, as well as other athletic activities that use muscles. An example of an athletic activity that is suitable for such muscle printing comparative analysis can include the firing of an arrow from a bow, which includes a draw-hold, release muscle performance profile, which can be considered a noncontinuous muscle activity. FIGS. 3A-3D show the graphical output of for an individual and then the comparison of the individual with one or more other individuals.

FIG. 3A includes a graph that illustrates sEMG amplitude versus time of a subject during a muscleprint exercise routine that has an action-hold-release protocol, and is exemplified by a using a bow to draw-hold-release. This type of graph can be generated for substantially any muscle activity. While the X-axis identifies time at 10 seconds, the time can vary for any stage of the muscle activity. Also, the duration can be varied depending on the type of muscle activity.

FIG. 3B includes a graph that illustrates sEMG amplitude versus time of two different subjects during a muscleprint exercise routine that has an action-hold-release protocol, and is exemplified by a using a bow to draw-hold-release. Such a comparison can be done between individuals that know each other or random individuals. The second individual data can be obtained from a database or from a known other user.

FIG. 3C includes a graph that illustrates sEMG amplitude versus time of a subject compared to a database of subjects (e.g., similar subjects in size, weight, height age, condition, etc.) during a muscleprint exercise routine that has an action-hold-release protocol, and is exemplified by a using a bow to draw-hold-release. The database can be assessed over a network so that the individual can obtain the necessary information for the comparative analysis. The individual user can then select for similar users using a variety of criteria.

FIG. 3D includes a graph that illustrates sEMG amplitude versus time of a subject compared to an entire database of subjects during a muscleprint exercise routine that has an action-hold-release protocol, and is exemplified by a using a bow to draw-hold-release. The database can be continually updated by users providing their information to the database. The database can then be accessed by qualified users, such as the individual.

Figure 4A:
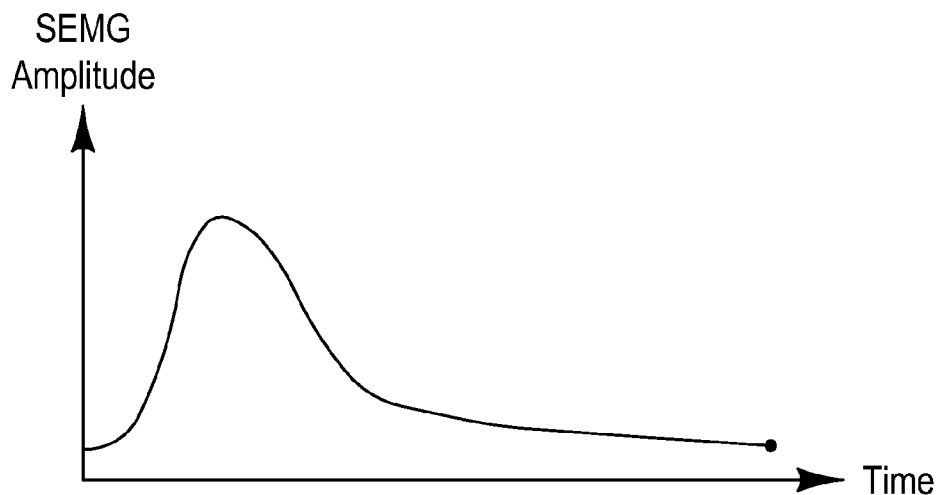
Figure 4B:
Figure 4C:
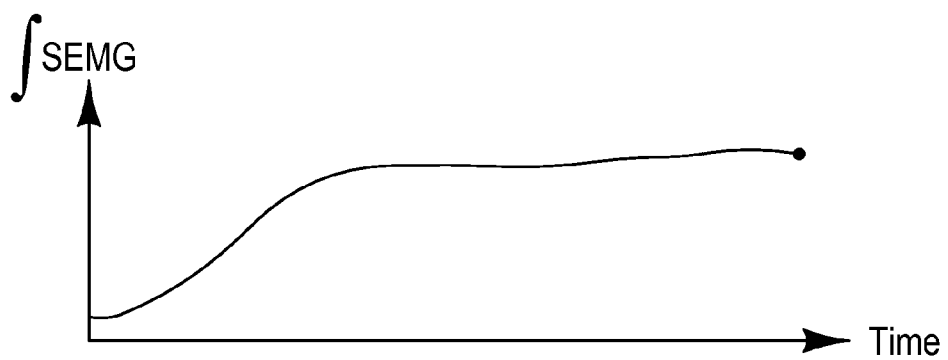
Figure 4D:
Figure 4E:
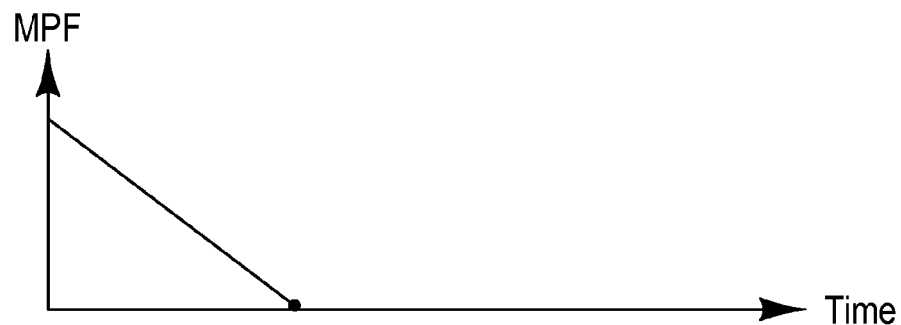

During the muscleprint, various types of data can be measured, recorded, and/or generated. The data can be relevant to various metrics that are useful for assessment of the muscle activity, or change in muscle activity. Some examples of the metrics that can be recorded or generated during the muscleprint protocol include the following: instantaneous rectified sEMG amplitude (see FIG. 4A); average rectified sEMG amplitude (see FIG. 4B); area under the sEMG graph/integrated sEMG (FIG. 4C); mean power frequency (MPF) (see FIG. 4D). While all of FIGS. 4A-4D illustrate metrics for a running muscle activity, FIG. 4E shows a weightlifting metric for MPF, which is visually different from for running. As such, the type of muscle activity can dictate the visual information of the graphical output. FIG. 4A includes a graph that illustrates sEMG amplitude versus time, where the sEMG amplitude is a metric observed during a muscleprint exercise routine such as walking, jogging, running, cycling, or the like. FIG. 4B includes a graph that illustrates sEMG amplitude versus time, where the sEMG amplitude is an average rectified amplitude during a muscleprint exercise routine such as walking, jogging, running, cycling, or the like. FIG. 4C includes a graph that illustrates sEMG amplitude versus time, where the sEMG amplitude is an integrated sEMG or area under curve of FIG. 4A during a muscleprint exercise routine such as walking, jogging, running, cycling, or the like. FIG. 4D includes a graph that illustrates mean power frequency (i.e., MPF) versus time, where the MPF may be a mean power frequency variance observed during a muscleprint exercise routine such as walking, jogging, running, cycling, or the like. FIG. 4E includes a graph that illustrates mean power frequency (i.e., MPF) versus time, where the MPF may be a mean power frequency variance observed during a muscleprint exercise routine such as "step-up" routine or weightlifting routine, or the like.

Figure 4F:
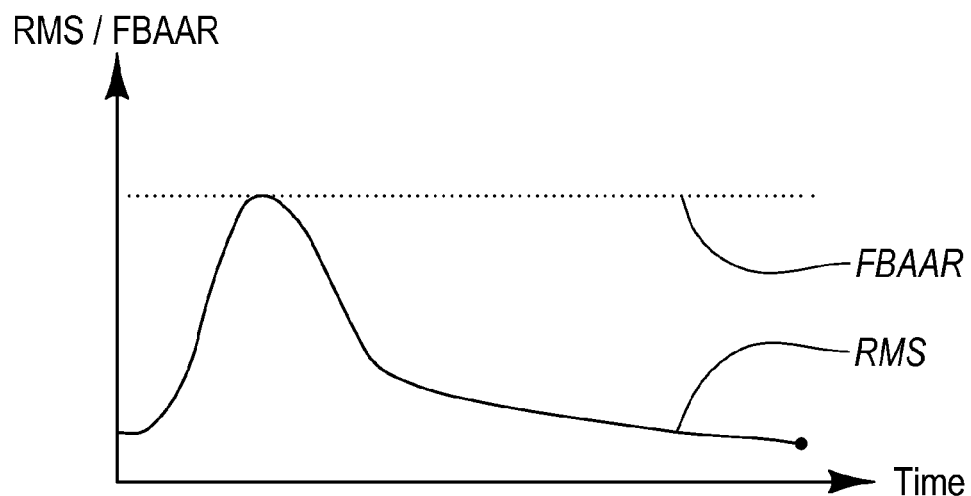

Additionally, the muscleprint protocol can obtain data that is then processed by a frequency-based amplitude adjusted RMS (FBAAR) process to create a standardized profile for an individual. The data can then be used to compare the beginning rectified amplitude values to the ending rectified amplitude values across time. For instance, a user may be able to make comparisons over the course of a particular period of time (e.g., 30 minute run) in which it is known that amplitude drop-off occurs despite speed/stride rate/incline being held constant (see FIG. 4F). FIG. 4F includes a graph that illustrates RMS sEMG versus time or frequency-based, amplitude-adjusted RMS sEMG versus time (i.e., FBAAR versus time) during a muscleprint exercise routine such as walking, jogging, running, cycling, or the like as well as noncontinuous muscle activities.

Additionally, the FBAAR process can be implemented with or substituted with time-based amplitude adjusted RMS (TBAAR). The TBARR is substantially similar to FBAAR in application to the invention described herein. As such, the amplitude adjustments can be made with any basis in addition to frequency and time. Any appropriate parameter may be amplitude adjusted using RMS. Thus, recitation herein of frequency-based amplitude adjusted RMS (FBAAR) process can also refer to TBAAR or other.

In one embodiment, the muscleprinting protocol can be implemented with computing devices and software. The computing device can be associated with sensors that are coupled to subject's body at particular locations. The sensors can be placed on the skin adjacent to one or more muscles to be monitored and assessed during the protocol. The sensor can be communicatively coupled, either wired or wireless, so a computing system having the software that can operate the method. The computing system can receive and record the data. The computing system, via muscleprinting protocol software, can process data from the sensors. The computing system can then generate a viewable format of the data for analysis by the subject. Additionally, the computing system can access a database over a network in order to obtain comparative data for one or more other users or to provide the subject's data to the database. The data from the database can be selectively filtered to identify one or more subjects that the subject may want to compare their data with. The other subjects may be persons known or unknown to the current subject undergoing the muscleprint. A viewable representation of the data, such as a graph, can then be generated to compare the current subject with one or more other subjects. The data of the current subject can also be provided to the database and stored, which data can then be accessed by other subjects for their own comparative analysis. Thus, the muscleprinting protocol can utilize computer hardware and/or software to automatically compare a subject's muscle response profile to a large database of muscle responses in order to categorize the subject's muscle fitness level. The protocol can also provide tailored exercise plans based on which muscles the subject could train for improvement. The protocol can also provide recommendations to a particular subject for training method to optimize muscle activity performance given their particular profile.

Figure 13:
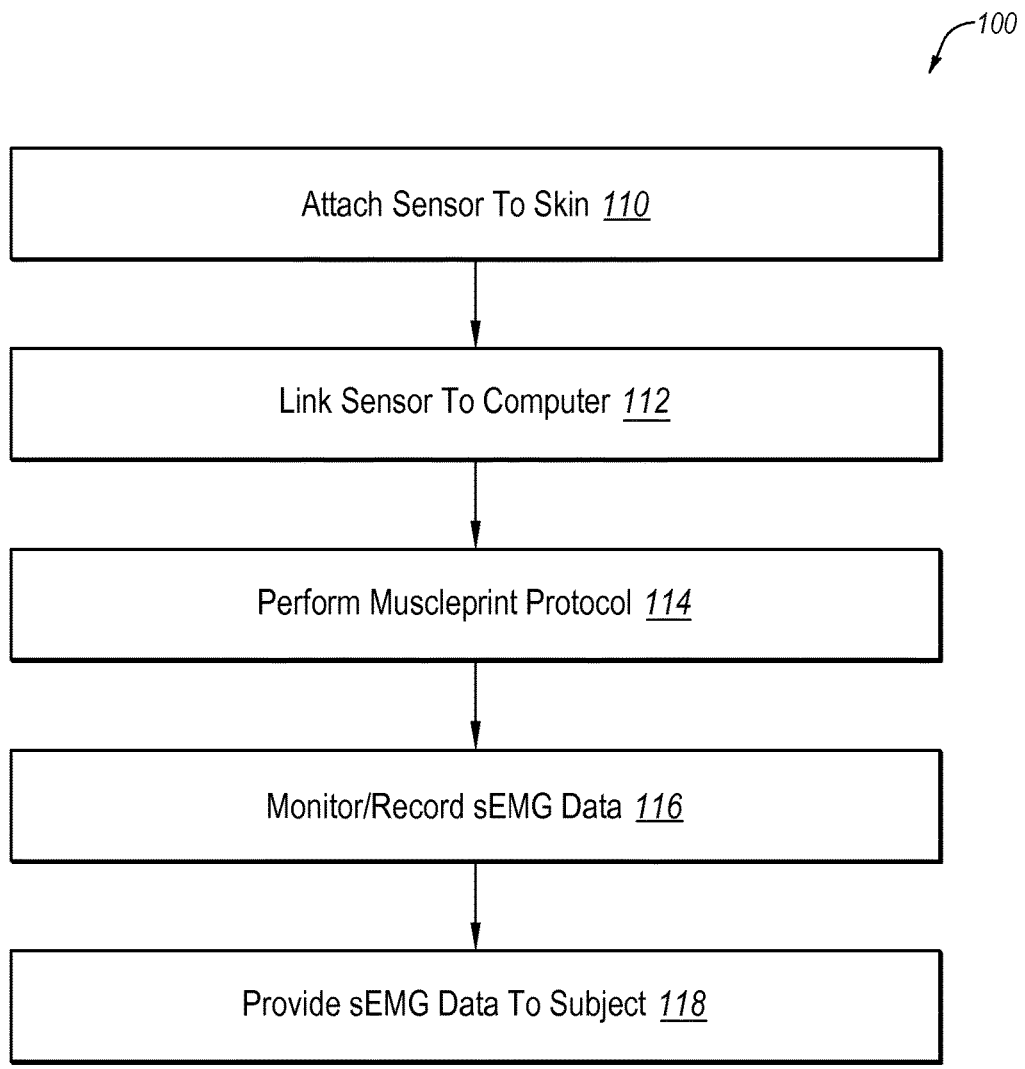

FIG. 13 illustrates an embodiment of a muscleprint protocol 100. Such a muscleprint protocol 100 can include: attaching one or more surface electromyometry (sEMG) sensors to the skin of a subject so as to be operably coupled with one or more muscles of the subject ("Attach Sensor To Skin," block 110); operably coupling the one or more sEMG sensors to a computing system ("Link Sensor To Computer," block 112); performing the predetermined muscle activity of a muscleprint protocol ("Perform Muscleprint Protocol," block 114), wherein in the muscleprint protocol the one or more sensors each monitor muscle sEMG data of the one or more muscles while the subject performs during the predetermined activity in order to determine the subject's muscular capabilities of the one or more muscles over a defined period of time or portion thereof; monitoring and/or recording sEMG data of the one or more muscles during the predetermined muscle activity ("Monitor/Record sEMG Data," block 116); and providing the sEMG data to the subject such that the subject can improve muscle performance for the predetermined muscle activity by using the sEMG data ("Provide sEMG Data to Subject," block 118).

In one embodiment, the muscleprint protocol can include determining and/or generating a muscle sEMG profile in response to the predetermined muscle activity over the defined period of time or portion thereof.

In one embodiment, the muscleprint protocol can include a step-up test that incrementally increases muscle output or muscle effort over one or more step-up time periods of the predetermined muscle activity until the subject is sufficiently fatigued or predetermined muscle activity time period or predetermined repetitions of the muscle activity.

In one embodiment, the muscleprint protocol can include graphing the muscleprint protocol with sEMG data versus time, and providing the graph to the subject.

In one embodiment, the muscleprint protocol can include accessing sEMG data of one or more other subjects from a database, and comparing the subject's sEMG data with the sEMG data of the other subjects from the database.

In one embodiment, the muscleprint protocol can include: filtering the one or more subjects from the database based on one or more criteria; providing sEMG data of the filtered one or more subjects to the computing system; and generating a graph of the subject's sEMG data with the sEMG data of the filtered one or more subjects.

The muscleprint protocol can be implemented as part of any of the other protocols described herein. Also, the method steps of the muscleprint protocol can be illustrated as a flowchart or the like.

Stride Rate Tuning

One of the reasons people exercise is due to the energy consumption by the body in order to perform an athletic activity. The energy consumption of exercise can be used for maintaining or improving a subject's physical attributes. During exercise, muscle contraction consumes energy. The more a muscle is contracted, the greater the energy consumption, which can be measured in calories. The energy consumption can also be expressed as work done by the muscle, and the more work done by the muscle does, the greater the energy consumption and greater amounts of calories are burned. Stride rate tuning can be used for any continuous muscle activity. Stride rate tuning can also be used for noncontinuous muscle activities when each repetition is described as a stride in accordance with the parameters herein.

Figure 5A:
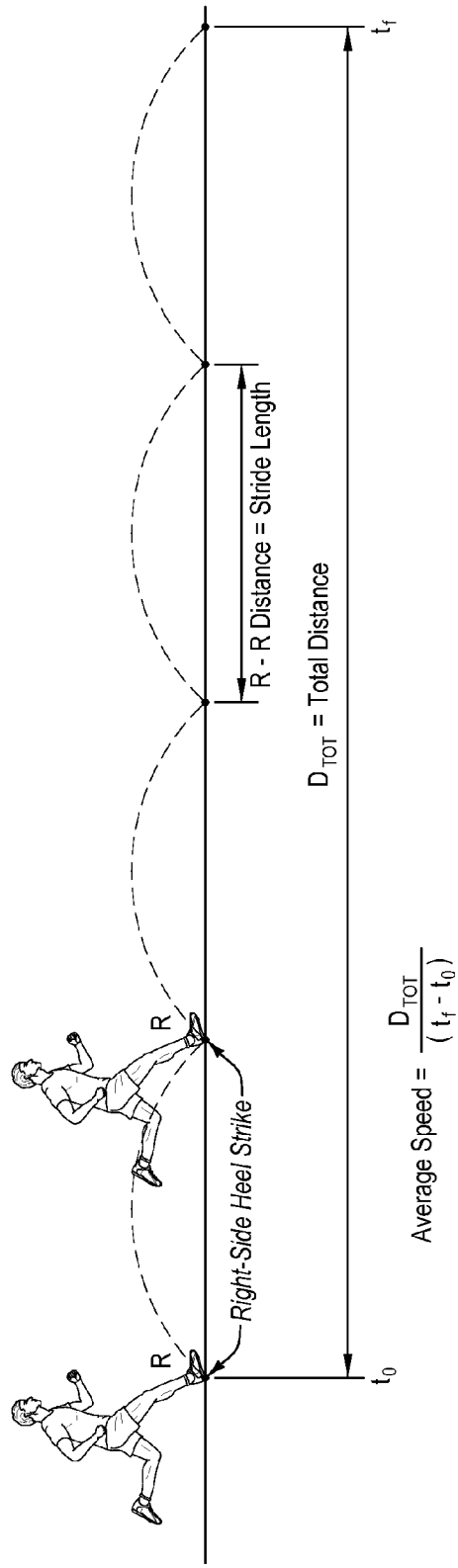
FIG. 5A includes a schematic representation of an exercise routine that is measured at stride length versus speed versus stride rate, wherein the stride length is measured as distance between right foot heal-strikes of a single stride.
Figure 5B:
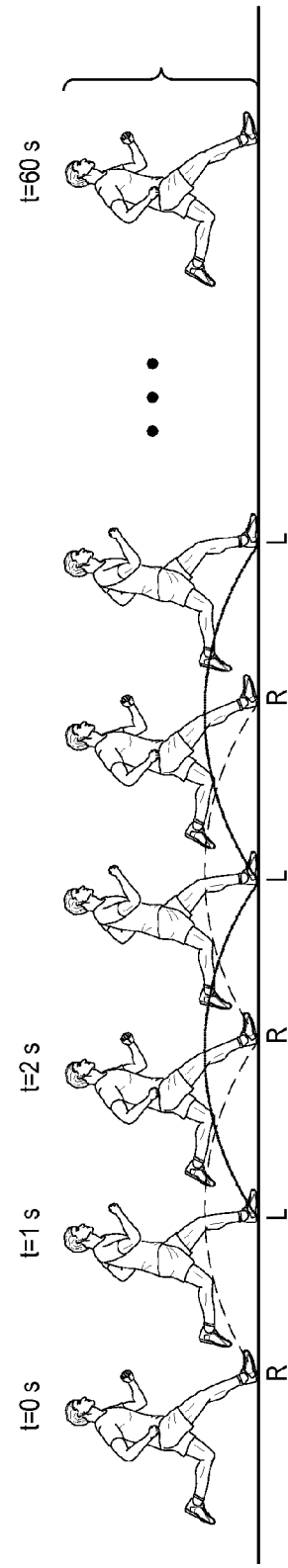
FIG. 5B includes a schematic representation of an exercise routine that is measured at half strides or for each heal strike of both feet.

Running is performed by contracting muscles during a stride. The rate at which a subject runs can be measured by the distance that is covered in a certain period of time. The subject's stride can be measured in terms of a stride rate that is the number of heel-strikes in a minute. For cycling, the stride can be measured in terms of when the peddle is at its lowest point. A heal-strike can be described as a beat, and the number of strikes over time can have a strike rate that can be described as "beats per minute" or "BPM." Also, stride length can be described as the distance covered in a single step by a runner. For cycling, the stride length can be the distance covered between peddle low points. It should also be noted that stride rate is not equivalent to speed. At a given constant speed, a subject may run at a variety of stride rates. In fact, for each athlete, there is a definite range of stride rates at any given speed. Also, runners are usually aware of a so-called "natural stride rate," even if they do not call it that, that they feel comfortable using at any given speed. FIG. 5A includes a schematic representation of an exercise routine that is measured at stride length versus speed versus stride rate, wherein the stride length is measured as distance between right foot heal-strikes of a single stride. FIG. 5B includes a schematic representation of an exercise routine that is measured at half strides or for each heal strike of both feet. The stride length is the distance between a first left or left foot heel-strike and a second right or left foot-heel strike, where only one foot is considered, which can be either the right foot or left foot as illustrated in FIG. 5A. The average speed can be determined by identifying the total distance (Dtot) traveled, which is divided by the total time. The total time can be determined by a final time (Tf) subtracted by the initial time (To). Equation 1 defines average speed.

$$\text{Average Speed} = Dtot/(Tf - To) \quad \quad \text{Equation 1}$$

The stride rate can be determined by using the heel-strikes of both the left and right foot. The total number of heel-strikes per minute equals the stride rate, which can be measured in beats per minute (BPM), which can be audible. It may also be referred to as heel-strikes per minute (hspm). Dividing the stride rate by two can provide the haploid stride rate, which is for one side of the body, right or left, which is shown in Equation 2.

$$\text{Haploid Stride Rate} = (\text{Stride Rate})/2 \quad \quad \text{Equation 2}$$

In the example illustrated in FIG. 5B, there are a total of 60 heel-strikes in 60 seconds, with one heel-strike per second. As such, the stride rate is 60 BPM (or hspm). The stride length cannot be determined from stride rate alone. Some form of distance information is needed for the calculation. The distance information, for example, can include stride length, total stride distance traveled, or other.

Different stride rates have different cumulative energy costs. A cumulative energy cost can be defined as being proportional to the sum of integrated rectified sEMG observed in major muscles being used for an activity. Equation 3 illustrates a calculation of a cumulative energy cost (CEC) for muscles that may be used for running, which can include: right quadriceps (A); left quadriceps (B); right hamstring (C); left hamstring (D); right calf (E); left calf (F); abdominal (G); and lower back (H). For example, for running, the cumulative energy cost could be proportional to the sum of the areas under the curves of rectified sEMG graphs recorded in the Left Quadriceps Femoris, Right Quadriceps Femoris, Left Hamstring, Right Hamstring, Left Gastrocnemius, and Right Gastrocnemius as shown in Equation 3. These muscles can each have in individual sensor associated therewith. However, the relationship can be simplified by selecting particular muscles as shown in Equations 4 or 5, which are only examples. Any muscle or group of muscles can be considered or excluded as desired. The area under the curve can then be used to calculate the calorie cost by using a skeletal muscle calorie index (SMCI).

$$CEC \propto \int A + \int B + \int C + \int D + \int E + \int F + \int G + \int H \quad \quad \text{Equation 3}$$

$$CEC \propto \int A + \int D + \int E + \int H \quad \quad \text{Equation 4}$$

$$CEC \propto \int A + \int B + \int C + \int D + \int E + \int F \quad \quad \text{Equation 5}$$

The SMCI can also be used as an adjustment to methods of calorie estimation currently in use which are based on heart rate. The SMCI adjustment can be used to improve the accuracy of the calculated calorie burn rate based on HR-only methods.

The stride rate can be used for stride rate tuning. Stride rate tuning (SRT) is can be described as a protocol for optimization stride rate of a subject based on sEMG data. The optimization of stride rate can be used to minimize energy expenditure during activities. There are various ways to implement SRT, one of which involves running at a constant speed. First, the runner applies sensors to their quads, hamstrings, and calves as well as other muscles such as those recited above (e.g., L and R leg muscles). A computing system having hardware and software can be programed to calculate the sum of the integrated sEMG amplitudes of all 6 muscles being monitored to determine the SEC. Then the runner begins to run at a constant rate. This can be done on a treadmill, or outside with some device that allows the runner to maintain their speed at a substantially constant rate. A secondary speed monitor can be used by the runner. A secondary speed monitor can include another object, such as a motorcycle, moped, car, bike or the like, that can operate at a constant speed, or use of a speedometer device that provides speed (e.g., audio or visual speed information) to the runner so that the runner can modulate their running to maintain the speed. During SRT, the runner should be on a flat or horizontal surface, or on a slope or incline that is substantially constant. The runner can run for a set duration (e.g., run for 20 minutes) to allow the observed rectified sEMG amplitude to level off, which can eliminate the need for FBAAR adjustment or any other amplitude adjusted RMS process, such as TBAAR. Then the stride rate is then varied, from the low limit of the runner's stride range to the high limit of the runner's stride range, in regular increments (see FIGS. 6A-6B).

For an example of SRT, the runner performs the following: 20 minutes of natural stride rate as a warm up; then 1 minute of running at 110 BPM; then 1 minute or running at 115 BPM; then 1 minute or running at 120 BPM; and so on up to resulting 1 minute of running at 190 BPM or maximum BPM for the runner. FIG. 6A includes a graph that illustrates stride rate versus time, where speed is constant throughout exercise routine at 5.5 MPH, where stride rate is held constant up to 20 minutes and then initially decreased before being increased in a step-up test. For this runner, 110-160 BPM is a stride rate range, and 130 BPM was self-identified as a "natural stride rate."

At the conclusion of the run, each increment has an associated combination rectified sEMG integral (e.g., area under the rectified sEMG curve for that increment for each muscle, then all muscles' integrals are added together) as shown in Equation 6, using the abbreviations for the leg muscles as shown above to calculate the cumulative integral (CI). The CI is then plotted verses time. Since the areas under the curves are proportional to the energy cost, the computing system can determine energy cost of different stride rates, and prepare graphical representations thereof (see FIG. 6B). FIG. 6B includes a graph that illustrates cumulative integral versus time for FIG. 6A, where speed is constant throughout exercise routine at 5.5 MPH in a "warm-up period." At 135 BPM, primary trough/valley observed, which is compared to the 130 self-identified "natural stride rate." At 155 BPM, secondary trough/valley observed, which is useful for running on an incline. Typical response profile for this type of graph is a "U" or "V" shaped curve.

The low-point on the graph of FIG. 6B corresponds to a stride rate which results in the smallest possible additive integral. This stride rate may not be equivalent to the stride rate that a user thinks of as their "natural stride rate". However, it is the stride rate which results in the smallest caloric burn rate, and as such is a singularly useful piece of information for competitive runners and can be referred to as the true natural stride rate. For noncontinuous muscle activities, a repetition can be considered to be a stride, and the method can be implemented for repetitions in place of strides. Thus, stride can also refer to repetitions of a muscle activity, such as weight lifting or arrow firing repetitions.

Figure 14:
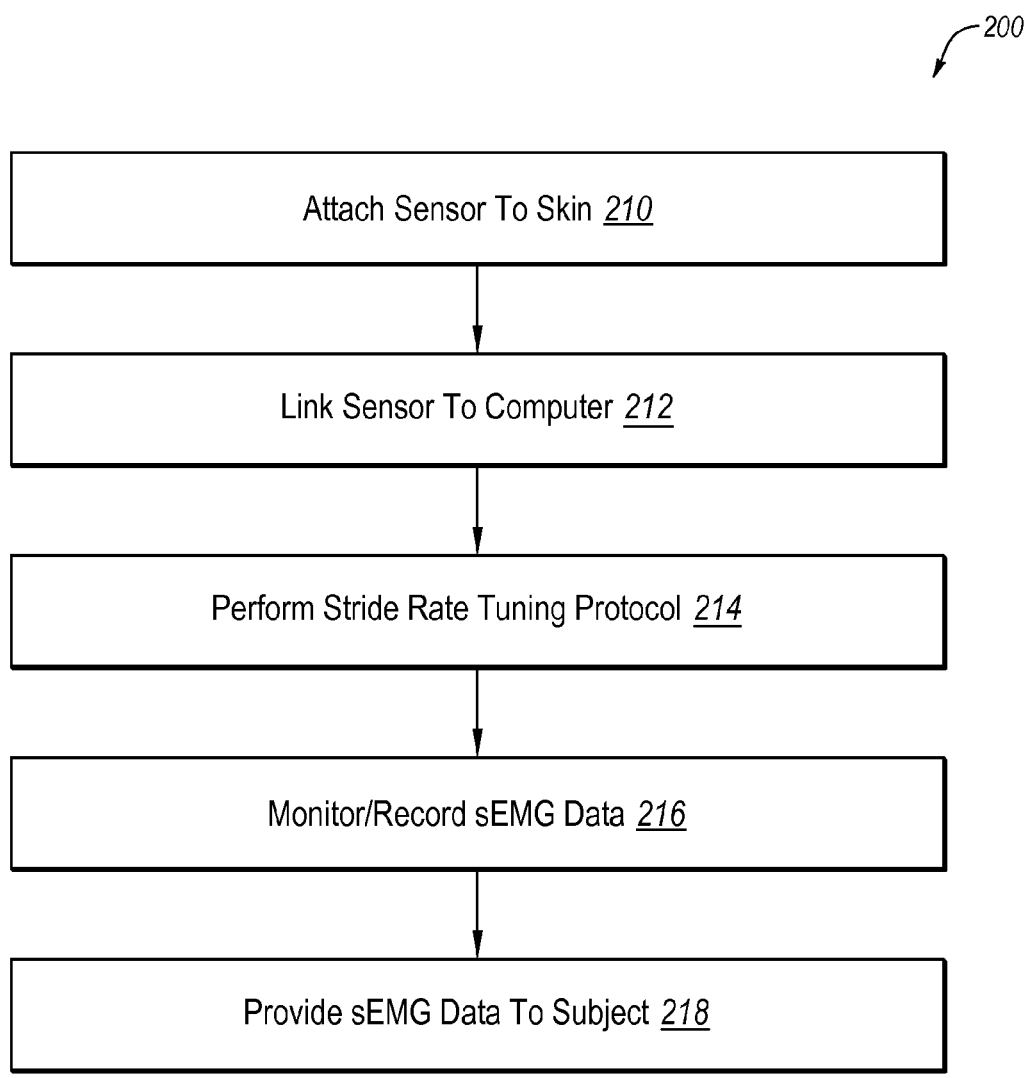

FIG. 14 illustrates an embodiment of performing a muscle improvement protocol 200 can include: attaching one or more surface electromyometry (sEMG) sensors to the skin of a subject so as to be operably coupled with one or more muscles of the subject ("Attach Sensor To Skin," block 210); operably coupling the one or more sEMG sensors to a computing system ("Link Sensor to Computer," block 212); performing the predetermined muscle activity of a stride rate tuning protocol ("Perform Stride Rate Tuning Protocol," block 214), wherein in the stride rate tuning protocol the one or more sensors monitor muscle sEMG data while the subject adjusts their caloric consumption during a controlled activity based on sEMG data that is measured and/or analyzed, and the sEMG data is provided to the subject in order to facilitate the adjustment of caloric consumption; monitoring and/or recording sEMG data of the one or more muscles during the predetermined muscle activity ("Monitor/Record sEMG Data," block 216); and providing the sEMG data to the subject such that the subject can improve muscle performance for the predetermined muscle activity by using the sEMG data ("Provide sEMG Data to Subject," block 218). The muscle improvement protocol can also include determining one or more of a stride; stride rate; natural stride rate; haploid stride rate; stride distance; or combination thereof. Also, the subject's true natural stride rate can be determined.

In one embodiment, the muscle improvement protocol can include determining cumulative energy cost for the one or more muscles. This information can then be used for optimizing stride rate for the subject based on sEMG data so as to minimize energy consumption by the one or more muscles.

In one embodiment, the muscle improvement protocol can include: performing the predetermined muscle activity at an initial constant rate or load for a predetermined time period or until exhaustion or until sEMG amplitude levels; performing the predetermined muscle activity at a low constant rate or load that is lower than the initial constant rate or load; and incrementally increasing the rate or load of the predetermined muscle activity at incremental time periods. The muscle improvement protocol can include the initial constant rate being substantially the subject's natural stride rate or estimate thereof.

In one embodiment, the muscle improvement protocol can include: computing energy costs of different stride rates; and providing the computed energy costs to the subject.

The stride rate protocol can be implemented as part of any of the other protocols described herein. Also, the method steps of the stride rate protocol can be illustrated as a flowchart or the like.

Controlled Activity Training (CAT)

Additionally, sEMG data can be used in controlled activity training for improvement of muscle function and endurance. Controlled activity training (CAT) refers to performing an activity with some manner of control with regard to sEMG data. In one instance, sEMG data is provided to the subject so that they can modulate their muscle activity in order to maintain or attempt to maintain the sEMG data at a certain level. In another instance, it includes using sEMG data to determine at what time point during a muscle activity fatigue sets in that reduces caloric consumption, and then the subject attempts maximum muscle activity output for a period up to the time point when muscle activity fatigue begins to set in. In both cases, muscle activity is controlled by use of sEMG data. As such, the sEMG data can include control variables as follows: sEMG amplitude; integrated sEMG; MPF; and muscle fatigue onset index (MFOI). The subject can then use these control variables in order to modulate the muscle activity, which can include modulating the following dependent variables: speed; stride rate; stroke rate (swimming); or weight lifted. Of course, the muscle activity that is a dependent variable will depend on the type of physical activity.

Figure 7A:
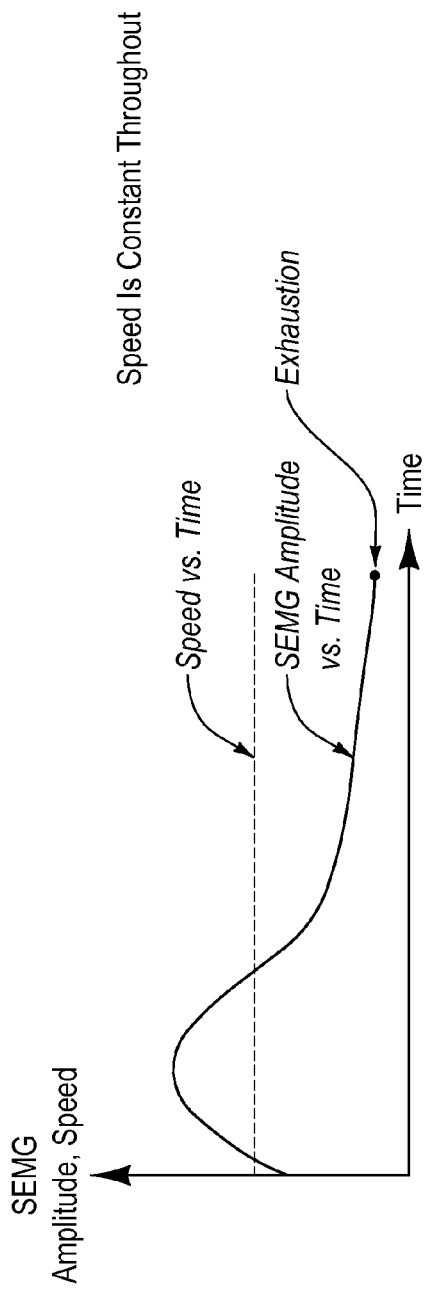
FIG. 7A includes a graph that illustrates sEMG amplitude versus time or speed versus time, where speed is constant throughout exercise routine.
Figure 7B:
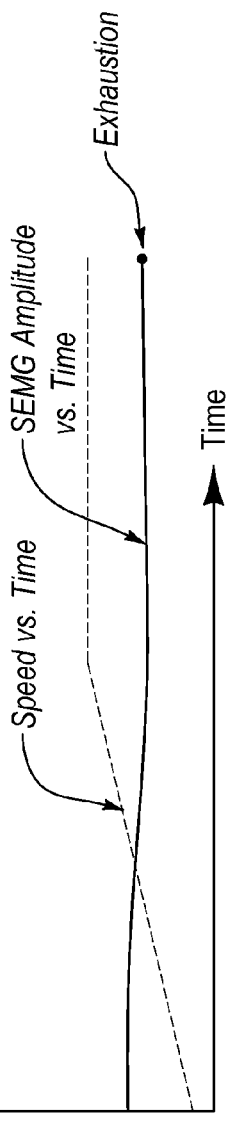
FIG. 7B includes a graph that illustrates sEMG amplitude versus time or speed versus time, where speed is controlled to keep sEMG amplitude under a limit throughout exercise routine, and exhaustion is delayed.

For example, it has been observed that when running for certain time (e.g., 30 minutes), the amplitude of rectified sEMG observed in major muscle groups of the lower extremities initially demonstrates a large peak which decreases over the course of the first period (e.g., 10-20 minutes) of the run, but which can vary depending on the subject (see FIG. 7A). FIG. 7A includes a graph that illustrates sEMG amplitude versus time or speed versus time, where speed is constant throughout exercise routine. Then, the amplitude continues to decrease thereafter until the end of the run, but at a much slower rate of decrease. The first period (e.g., 12 minutes) of the run have a greater caloric cost than the remainder of the run. The rectified sEMG amplitude, however, can be reduced by reducing the speed of the run. If the runner's speed is allowed to be variable, and instead hold the rectified sEMG amplitude constant (e.g., at whatever level is observed toward the end of an initial calibration run), the runner's speed would start out slow, and gradually speed up as their muscles physical properties changed over the course of the run. This specific implementation of CAT is called Delayed Fatigue Onset Training (DFOT). DFOT is a process which realizes at its core that the energy available to an individual during an activity is limited. The calories available to that individual are limited. The total work that the individual can do during the activity is limited. Since energy expenditure is proportional to sEMG output, by reducing the early-stage sEMG output, the runner can reduce the high caloric cost of the first period (e.g., 12 minutes) of a run. These calories are therefore available to the runner at the end of the run (see FIG. 7B). FIG. 7B includes a graph that illustrates sEMG amplitude versus time or speed versus time, where speed is controlled to keep sEMG amplitude under a limit throughout exercise routine, and exhaustion is delayed.

While DFOT is one type of CAT, the subject may also take the opposite approach, and design a CAT focused on maximizing caloric burn with respect to time. A runner who is interested in burning as many calories as quickly as possible or having a goal of weight loss and fitness, or short muscle activity competitive performance, but not endurance, might be interested in a CAT structured as follows. The runner goes on initial calibration run and the sEMG amplitude is measured. The inflection point is measured, and the time to the inflection point is saved. On the next run, the runner warms up with muscle groups other than those of their lower extremities (some weight-lifting, for instance, to get the heart rate elevated for ten minutes prior to the run). Then, the runner engages in interval training where the length of the intervals are equivalent to the length of time until the inflection point. Let us assume for example that the inflection point is located at 12 minutes. The runner would be instructed to run near their maximum comfortable speed for 12 minutes, without the benefit of accelerating into that speed. Next, the runner takes a break for ten minutes, perhaps working out with different exercises (weight-lifting). Then, the runner goes back and runs another interval period (e.g., 12 minutes) at a fast pace. Each time the runner performs the interval run, they can maximize caloric consumption by starting the muscle activity of running as hard and fast as possible for the first period (e.g., 12 minutes), and then doing a different activity after the first period and/or between running periods when the amplitude starts to drop and caloric burn rate decreases (see FIG. 8A).

Figure 8A:
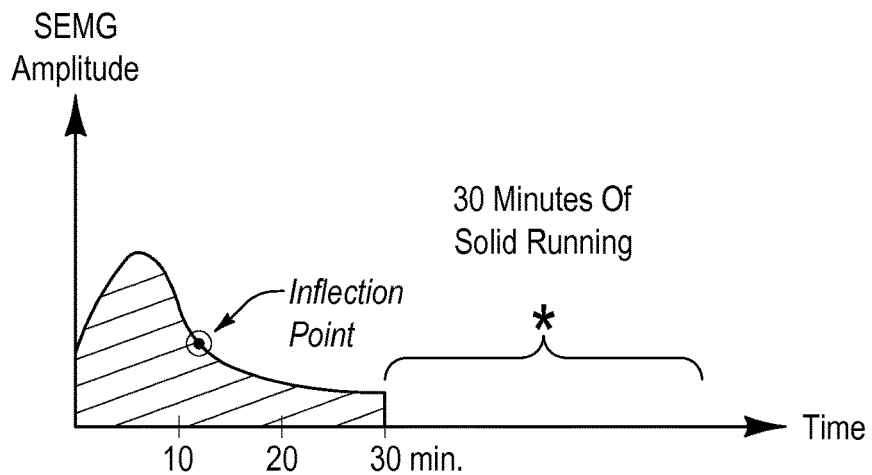
FIG. 8A includes a graph that illustrates sEMG amplitude versus time for a set time of consistent exercise (e.g., running etc.) followed by rest or non-exercise, where an inflection point is identified.

FIG. 8A includes a graph that illustrates sEMG amplitude versus time for a set time of consistent exercise (e.g., running etc.) followed by rest or non-exercise, where an inflection point is identified. In this figure, the runner runs at a solid effort for 30 minutes, followed by some period of rest before again running solid for another period of time.

Figure 8B:
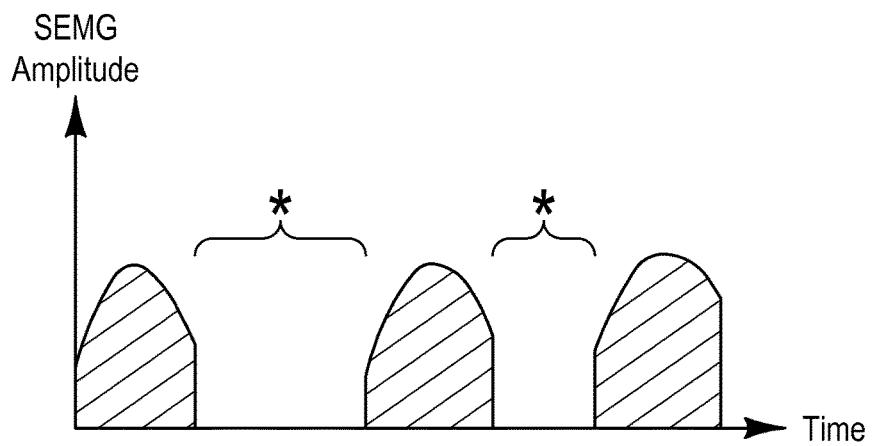
FIG. 8B includes a graph that illustrates sEMG amplitude versus time for a set time of consistent exercise (e.g., weight lifting or other periodic exercise) followed by rest or non-exercise, which is shown as exercise-rest-exercise-rest-exercise.
Figure 8C:
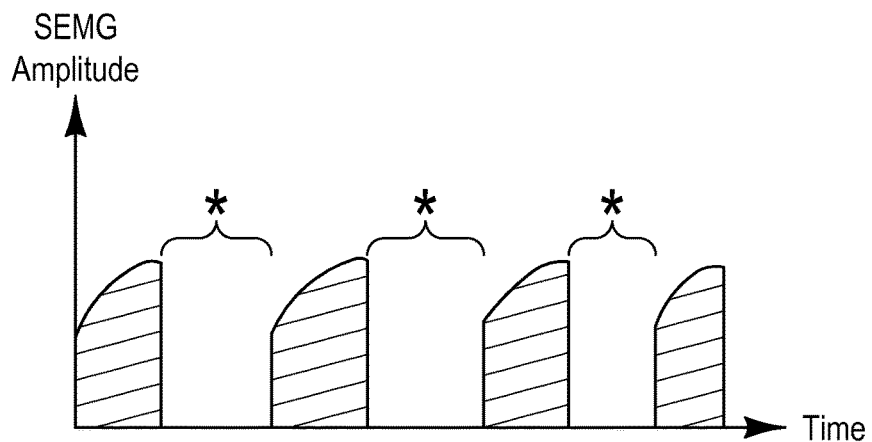
FIG. 8C includes a graph that illustrates sEMG amplitude versus time for a set time of consistent exercise (e.g., weight lifting or other periodic exercise) followed by rest or non-exercise, which is shown as exercise-rest-exercise-rest-exercise, where

Also, these CAT protocols can be performed with any muscle activity. Weightlifting is an example of a noncontinuous muscle activity. FIG. 8B includes a graph that illustrates sEMG amplitude versus time for a set time of consistent exercise (e.g., weight lifting or other periodic exercise) followed by rest or non-exercise, which is shown as exercise-rest-exercise-rest-exercise. FIG. 8C includes a graph that illustrates sEMG amplitude versus time for a set time of consistent exercise (e.g., weight lifting or other periodic exercise) followed by rest or non-exercise, which is shown as exercise-rest-exercise-rest-exercise. FIG. 8C is an alternative profile compared to FIG. 8B, where FIG. 8B shows a rounded profile indicative of a extending the set past the maximum, FIG. 8C show that the set is terminated at the maximum.

Additionally, another CAT protocol for DFOT can be implemented as follows. The runner first goes on a calibration run for a first period of time (e.g., 12 minutes) in which the rectified sEMG amplitude is measured and the inflection point is identified. The inflection point marks a change from initial high-amplitude levels to post first period (e.g., post-12-minute) lower-amplitude levels. The amplitude at the inflection point is measured, and the final amplitude is measured, as well as at any time point therebetween. The average amplitude is calculated for the post-inflection point data. The average amplitude level (post-inflection) is recorded and may be analyzed and/or graphed or otherwise provided to the runner. The runner than goes on another run, and uses the average amplitude level that is saved as the maximum allowable amplitude level for the whole run. Accordingly, amplitude is held constant or substantially constant during the whole next run. If the amplitude is too high, the runner's speed can be decremented or otherwise reduce until the amplitude is below the maximum allowable amplitude level (e.g., safety limit) Amplitude being lower than the limit is permissible.

Figure 15:
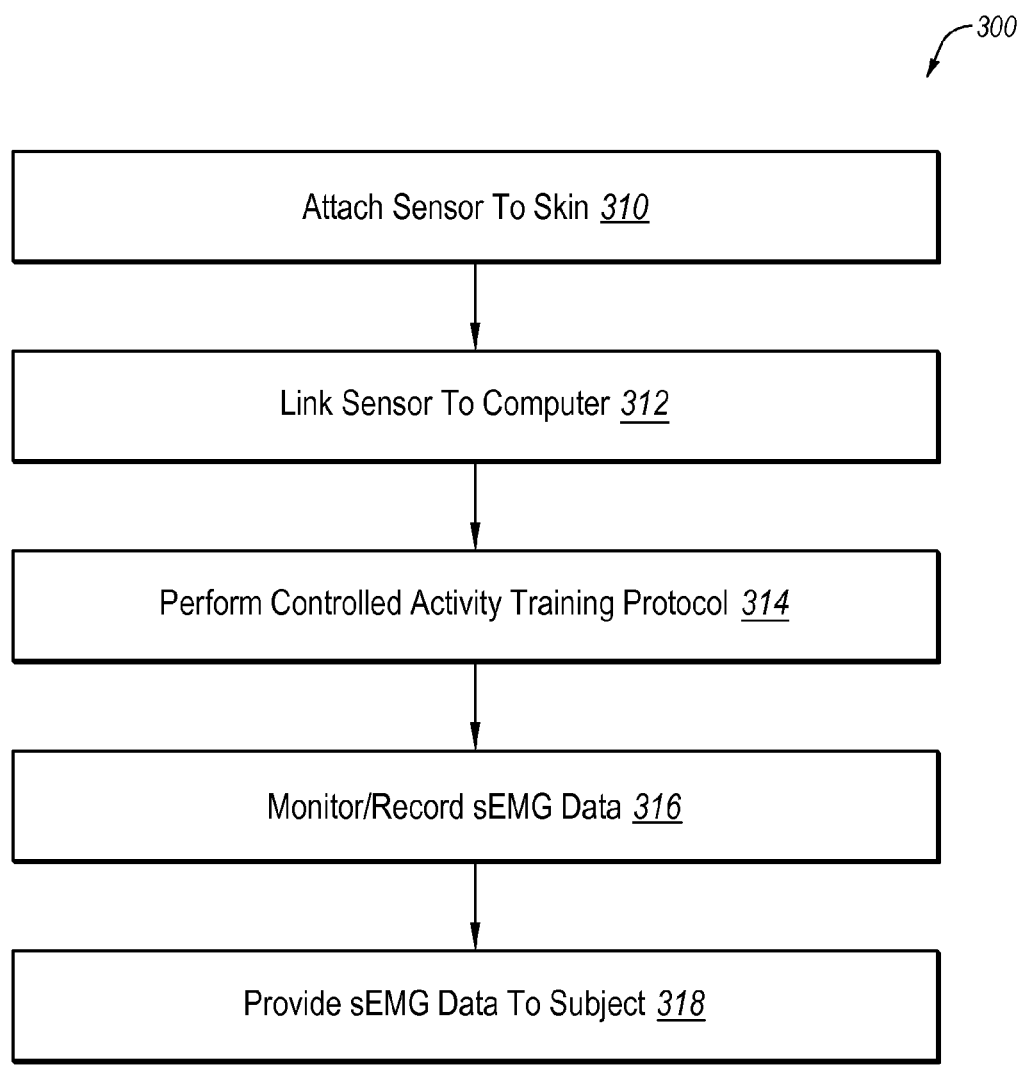

FIG. 15 illustrates an embodiment of a muscle improvement protocol 300, which can include: attaching one or more surface electromyometry (sEMG) sensors to the skin of a subject so as to be operably coupled with one or more muscles of the subject ("Attach Sensor to Skin," block 310); operably coupling the one or more sEMG sensors to a computing system ("Link Sensor to Computer," block 312); performing the predetermined muscle activity of a controlled activity training protocol ("Perform Controlled Activity Training Protocol," block 314), wherein in the controlled activity training protocol the subject maintains substantially a constant sEMG metric or metric derivative or metric integral by varying muscle activity exertion during the predetermined muscle activity; monitoring and/or recording sEMG data of the one or more muscles during the predetermined muscle activity ("Monitor/Record sEMG Data," block 316); and providing the sEMG data to the subject such that the subject can improve muscle performance for the predetermined muscle activity by using the sEMG data ("Provide sEMG Data to Subject," block 318).

In one embodiment, the muscle improvement protocol can include: analyzing the sEMG data; and determining a fatigue initiation time point at which fatigue initiates after an initial time period.

In one embodiment, the muscle improvement protocol can include performing the predetermined muscle activity again for a time period less than the initial time period so that the subject ceases performance of the predetermined muscle activity before the fatigue initiation time point. This can include controlling a second performance of the predetermined muscle activity based on sEMG data collected during a first performance of the predetermined muscle activity.

In one embodiment, the muscle improvement protocol can include: holding substantially constant for control variables selected from sEMG amplitude, integrated sEMG, MPF, and MFOI; and varying performance of the predetermined muscle activity at the substantially constant control variable. The muscle improvement protocol can also include performing a delayed fatigue onset training protocol.

In one embodiment, the muscle improvement protocol can include: performing a calibration protocol for the predetermined muscle activity; determining an inflection point of sEMG data during the calibration protocol, wherein the inflection point identifies an activity period from beginning the calibration protocol to a fatigue time point; and performing the predetermined muscle activity for the activity period one or more times. Also, prior to performance of the predetermined muscle activity after the calibration protocol, the subject can warm up with muscle groups other than involved in the predetermined muscle activity. The activity period can be performed at a maximum effort that can be substantially sustained for the duration of the activity period. Activity between the different activity periods can include either resting or performing a muscle activity different from the predetermined muscle activity for a rest period between repetitions of the predetermined muscle activity. Activity during the activity period can be performed so as to maximize caloric consumption during the activity period.

In one embodiment, the muscle improvement protocol can include: measuring sEMG amplitude at inflection point; measuring final amplitude of predetermined muscle activity; calculating average sEMG amplitude for post-inflection point data; and performing the predetermined muscle activity another time while holding the sEMG amplitude substantially constant.

The controlled activity protocol can be implemented as part of any of the other protocols described herein. Also, the method steps of the controlled activity training protocol can be illustrated as a flowchart or the like.

Frequency-Based, Amplitude-Adjusted Root Mean Square (FBAAR)

It has been experimentally observed that when a subject exercises for a long period of time (e.g., t>10 minutes) there is noticeable sEMG amplitude drop-off which occurs in the rectified sEMG signals of their muscles (see FIGS. 10A-10C. For example, if someone runs for a period of time (e.g., 30 minutes), the amplitude of rectified sEMG observed will decrease noticeably over this period of time. In one aspect, it can be useful to adjust the amplitude of the rectified signal so that this decrease is cancelled out. This can be done by providing the sEMG data to the subject so that they can module effort. The amplitude drop-off correlates with muscle fatigue (e.g., compression of power spectrum), though the rate of fatigue, and the correlation, is subject-specific.

FIG. 10A includes a graph similar to FIG. 8A, which shows the sEMG amplitude profile. FIG. 10B includes a graph that illustrates sEMG amplitude versus frequency for a non-fatigued muscle spectrum from FIG. 10A, and shows the MPF. FIG. 10C includes a graph that illustrates sEMG amplitude versus frequency for a fatigued muscle spectrum from FIG. 10A, and shows the MPF.

Figure 9A:
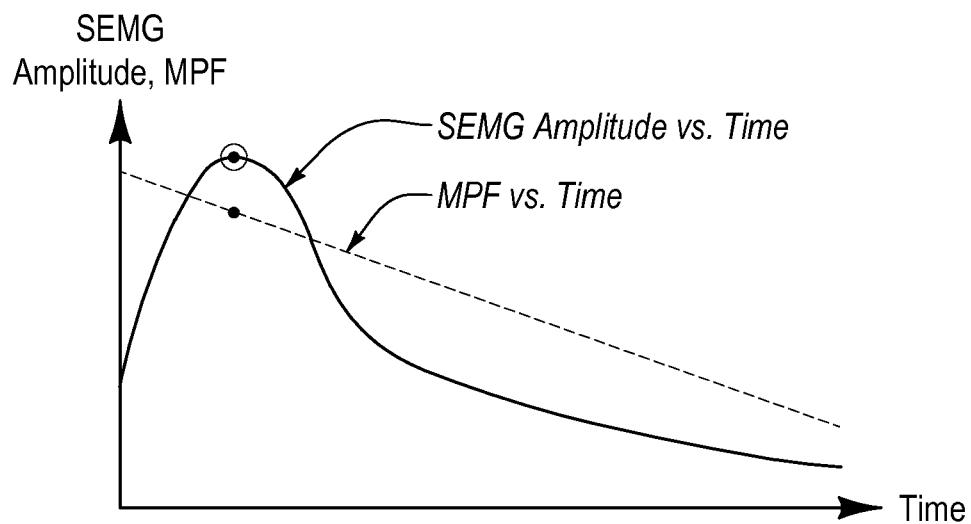
FIG. 9A includes a graph that illustrates sEMG amplitude versus time or MPF versus time of a subject during an exercise routine that is conducted as a constant rate, such as 5.5 MPH with a 135 BPM stride rate, where data can be from left quad.
Figure 9B:
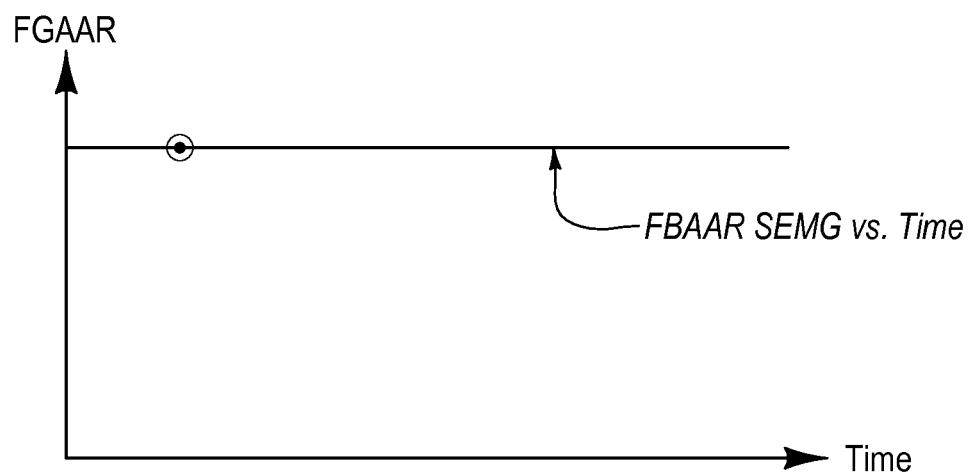
FIG. 9B includes a graph that illustrates frequency-based, amplitude-adjusted RMS sEMG versus time (i.e., FBAAR v. time) of a subject during an exercise routine that is conducted as a constant rate, such as 5.5 MPH with a 135 BPM stride rate, where data can be from left quad.

Also, a FBAAR muscle activity protocol can include a subject first performing a typical exercise, and the computing system establishes the correlation between degree of amplitude drop-off over time, and the corresponding MPF (see FIG. 9A). Then, in the future, when the subject performs similar types of exercises, the computing system can measure or determine the MPF for the subject, and the subject can modulate their muscle activity in order to adjust the signal accordingly (see FIG. 9B). This provides the subject with a way to observe the amplitude levels that would be observed if the subject were always minimally fatigued with respect to the muscle potential. When attempting to compare and correlate amplitude levels for a subject over time, or over multiple days, this muscle activity protocol can be useful for the standardization and comparison of amplitude of values.

The FBAAR muscle activity protocol can improve fitness and endurance, and can be used to help a subject to delay the onset of fatigue. By repeating the protocol, a subject can extend the period time they can exercise before the onset of fatigue. The computing system can implement algorithms in order to make use of metrics, which are provided to the subject during the protocol so that they can adjust their muscle activity output.

In one embodiment, a muscle assessment protocol can include: attaching one or more surface electromyometry (sEMG) sensors to the skin of a subject so as to be operably coupled with one or more muscles of the subject; operably coupling the one or more sEMG sensors to a computing system; performing the predetermined muscle activity of an amplitude-adjusted root mean square protocol, wherein in the frequency-based, amplitude-adjusted root mean square that includes displaying sEMG data that is adjusted to compensate for muscle fatigue of the one or more muscles; monitoring and/or recording sEMG data of the one or more muscles during the predetermined muscle activity; and providing the sEMG data to the subject such that the subject can improve muscle performance for the predetermined muscle activity by using the sEMG data. Also, the protocol can include: providing an sEMG metric to the subject during the predetermined muscle activity; and modulating effort by the subject during the predetermined muscle activity so as to maintain the sEMG metric at substantially a constant.

The FBAAR muscle activity protocol can be implemented as part of any of the other protocols described herein. Also, the method steps of the FBAAR muscle activity protocol can be illustrated as a flowchart or the like.

In one embodiment, the invention described herein can be implemented with the sensors or systems described in U.S. Provisional Application Nos. 61/385,048 and 61/514,148 and U.S. patent application Ser. No. 13/239,033. Additionally, the invention described herein can be implemented with metrics and algorithms described in U.S. Provisional Patent Application No. 61/385,038 and U.S. patent application Ser. No. 13/239,064. Also, the invention described herein can be implemented with methods of promoting fitness described in U.S. Provisional Application No. 61/385,053 and U.S. patent application Ser. No. 13/239,079. Further, the invention described herein can be implemented with graphing methods described in U.S. Provisional Application No. 61/385,049. Also, the invention described herein can be implemented with the multi-functional carrying case and associated biometric sensors and transceivers described in U.S. Provisional Application No. 61/385,051. The invention described herein can be implemented with the devices, systems, and/or methods described in U.S. Pat. Nos. 7,593,769 and 7,809,435. The patents and patent applications recited herein are incorporated herein by specific reference in their entirety.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. The methods can also be implemented with hardware and/or software on the sensors and/or computing system or other means for performing the methods disclosed herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, and hand-held computing systems as well as any other computing device.

There is little distinction left between hardware and software implementations of aspects of systems; the use of hardware or software is generally (but not always, in that in certain contexts the choice between hardware and software can become significant) a design choice representing cost versus efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 11:
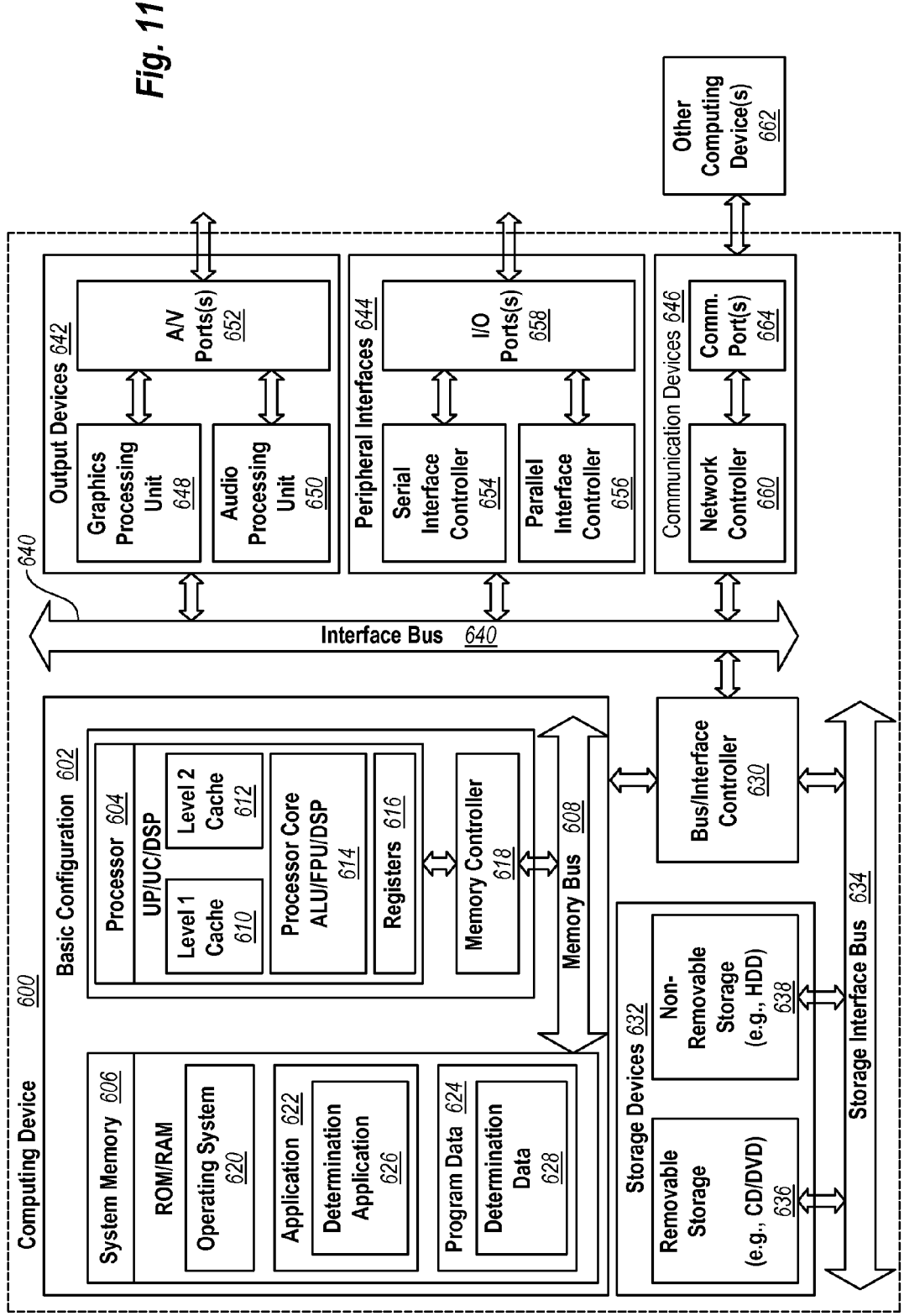
FIG. 11 includes a schematic representation of a computing system that can be used in the systems and methods of the present invention.

FIG. 11 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 6 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A muscle assessment protocol comprising:
    a computer system communicating with one or more surface electromyometry (sEMG) sensors attached to skin of a subject so as to be operably coupled with one or more muscles of the subject;
    the computing system monitoring and/or recording sEMG data of the one or more muscles during a predetermined muscle activity of the muscle assessment protocol that includes a frequency-based or amplitude-adjusted root mean square protocol; and
    the computing system providing the sEMG data to the subject such that the subject can improve muscle performance for the predetermined muscle activity by using the sEMG data.

2. The muscle assessment protocol of claim 1, wherein the predetermined muscle activity includes static loading resistance or dynamic muscle use.

3. The muscle assessment protocol of claim 1, wherein the predetermined muscle activity is provided to the subject by the computing system.

4. The muscle assessment protocol of claim 1, wherein the predetermined muscle activity includes a continuous exercise routine, a noncontinuous exercise, or routine.

5. The muscle assessment protocol of claim 4, wherein the continuous exercise routine includes one or more of walking, jogging, running, sprinting, hiking, cycling, rollerblading, roller skating, skiing, cross-country skiing, rowing, swimming, snowboarding, yoga, pilates, or the like.

6. The muscle assessment protocol of claim 4, wherein the noncontinuous exercise routine includes one or more of firing an arrow from a bow, weightlifting, golf swing, bat swing, ball throw, punch, kick, jumping, squatting, or the like.

7. The muscle assessment protocol of claim 1, wherein:
    the frequency-based, amplitude-adjusted root mean square step includes displaying sEMG data that is adjusted to compensate for muscle fatigue of the one or more muscles.

8. The muscle assessment protocol of claim 1, wherein the sEMG data is a metric selected from: sEMG amplitude; instantaneous rectified sEMG amplitude; average rectified sEMG amplitude; area under sEMG curve; area over sEMG curve; integrated sEMG; derivative sEMG; frequency-based, amplitude adjusted RMS sEMG; mean power frequency (MPF); muscle fatigue onset index (MFOI); and/or combination thereof.

9. The muscle assessment protocol of claim 1, further comprising:
    obtaining ECG data; and
    using the ECG data in conjunction with the sEMG data.

10. A muscle assessment protocol comprising:
    a computing system communicating with one or more surface electromyometry (sEMG) sensors attached to skin of a subject so as to be operably coupled with one or more muscles of a subject;
    the one or more sEMG sensors being configured to be operably coupled to the computing system while a subject performs a predetermined muscle activity of an amplitude-adjusted root mean square protocol, wherein the frequency based, amplitude-adjusted root mean square protocol includes displaying sEMG data that is adjusted to compensate for muscle fatigue of the one or more muscles;
    monitoring and/or recording sEMG data of the one or more muscles during the predetermined muscle activity; and
    providing the sEMG data to the subject such that the subject can improve muscle performance for the predetermined muscle activity by using the sEMG data.

11. The muscle assessment protocol of claim 10, further comprising:
    providing an sEMG metric to the subject during the predetermined muscle activity; and
    modulating effort by the subject during the predetermined muscle activity so as to maintain the sEMG metric substantially at a constant.

12. The muscle assessment protocol of claim 10, further comprising a static muscle activity that occurs with no load or with an isometric load.

13. The muscle assessment protocol of claim 12, further comprising a static muscle activity evaluation.

14. The muscle assessment protocol of claim 13, wherein the static muscle activity evaluation includes observation of a rectified amplitude of the sEMG data.

15. The muscle assessment protocol of claim 14, wherein the static muscle activity evaluation is observed for a specific muscle or muscle group or as a comparison to other muscles or muscle groups.

16. The muscle assessment protocol of claim 10, wherein absolute levels of the sEMG data is monitored through root mean square of the sEMG amplitude.

17. The muscle assessment protocol of claim 10, wherein abnormally large values of RMS sEMG are identified or determined.

18. The muscle assessment protocol of claim 10, wherein rhythmic contraction patterns of the muscle or muscle groups are identified or determined and are based on rectified amplitude.

19. The muscle assessment protocol of claim 10, wherein during an isometric loading protocol, the subject exerts an amount of force while keeping a limb fixed in a single position.

20. The muscle assessment protocol of claim 19, wherein:
    force exerted is measured as a fixed percentage of Maximum Voluntary Contraction (MVC) and a median frequency (MF) or mean power frequency (MPF) is measured or determined by observing or analyzing a frequency spectrum of sEMG.

21. The muscle assessment protocol of claim 10, wherein:
    a fatigue level of muscles is established and a point at which fatigue begins to occur is identified.

22. A system for performing a muscle assessment protocol comprising:
    one or more surface electromyometry (sEMG) sensor means configured to be attached to skin of a subject so as to be operably coupled with one or more muscles of the subject;
    computing means configured to be operably coupled the one or more sEMG sensor means;
    the computing means further configured to display sEMG data that is adjusted to compensate for muscle fatigue of the one or more muscles when the subject performs a predetermined muscle activity of an amplitude-adjusted root mean square protocol;
the computing means further configured to monitor and/or record sEMG data of the one or more muscles during the predetermined muscle activity.

* * * * *